(12) United States Patent
Abraham et al.

(10) Patent No.: US 9,782,475 B2
(45) Date of Patent: *Oct. 10, 2017

(54) METHOD OF TREATING FOOD ALLERGIES BY ADMINISTERING A NANOPARTICLE COMPRISING HEPARIN AND CHITOSAN ENCAPSULATING IL-12

(71) Applicant: Duke University, Durham, NC (US)

(72) Inventors: Soman Abraham, Chapel Hill, NC (US); Kam Leong, Durham, NC (US); Herman Staats, Cedar Grove, NC (US); Ashley St. John, Durham, NC (US)

(73) Assignee: Duke University, Durham, NC (US)

( * ) Notice: Subject to any disclaimer, the term of this patent is extended or adjusted under 35 U.S.C. 154(b) by 252 days.

This patent is subject to a terminal disclaimer.

(21) Appl. No.: 14/336,411

(22) Filed: Jul. 21, 2014

(65) Prior Publication Data
US 2015/0023909 A1   Jan. 22, 2015

Related U.S. Application Data

(62) Division of application No. 13/252,516, filed on Oct. 4, 2011, now Pat. No. 8,802,076.

(60) Provisional application No. 61/389,457, filed on Oct. 4, 2010.

(51) Int. Cl.
| | |
|---|---|
| A61K 38/20 | (2006.01) |
| A61K 38/21 | (2006.01) |
| A61K 39/39 | (2006.01) |
| A61K 39/00 | (2006.01) |
| A61K 39/145 | (2006.01) |
| B82Y 5/00 | (2011.01) |
| A61K 38/19 | (2006.01) |
| A61K 9/51 | (2006.01) |
| A61K 39/085 | (2006.01) |
| A61K 39/12 | (2006.01) |

(52) U.S. Cl.
CPC .............. *A61K 39/39* (2013.01); *A61K 9/513* (2013.01); *A61K 9/5123* (2013.01); *A61K 38/191* (2013.01); *A61K 38/20* (2013.01); *A61K 38/2006* (2013.01); *A61K 38/208* (2013.01); *A61K 38/2013* (2013.01); *A61K 38/2066* (2013.01); *A61K 38/21* (2013.01); *A61K 39/0008* (2013.01); *A61K 39/085* (2013.01); *A61K 39/12* (2013.01); *A61K 39/145* (2013.01); *B82Y 5/00* (2013.01); *A61K 2039/5252* (2013.01); *A61K 2039/55505* (2013.01); *A61K 2039/55527* (2013.01); *A61K 2039/55555* (2013.01); *C12N 2760/16134* (2013.01); *Y10S 977/773* (2013.01); *Y10S 977/906* (2013.01)

(58) Field of Classification Search
CPC ... A61K 39/008; A61K 9/5123; A61K 38/208
See application file for complete search history.

(56) References Cited

U.S. PATENT DOCUMENTS

| | | | |
|---|---|---|---|
| 6,309,663 B1 | 10/2001 | Patel et al. | |
| 7,247,310 B1 | 7/2007 | Ohno et al. | |
| 7,304,045 B2 | 12/2007 | Sung et al. | |
| 8,802,076 B2 * | 8/2014 | Abraham | A61K 39/0008 424/85.2 |
| 2001/0051189 A1 | 12/2001 | Fernandez et al. | ........... 424/499 |
| 2002/0172717 A1 | 11/2002 | Leong et al. | |
| 2006/0134785 A1 | 6/2006 | Fernandez et al. | ........... 435/375 |
| 2008/0095810 A1 | 4/2008 | Fernandez et al. | |
| 2008/0254078 A1 | 10/2008 | Kauper et al. | |
| 2010/0015050 A1 | 1/2010 | Panyam et al. | |

FOREIGN PATENT DOCUMENTS

| | | |
|---|---|---|
| WO | 98/01160 | 1/1998 |
| WO | 2007/042572 | 4/2007 |
| WO | 2008/039390 | 4/2008 |
| WO | 2009/051837 | 4/2009 |

OTHER PUBLICATIONS

Aubin-Tam et al., "Gold Nanaparticie-Cytochrome c Complexes: The Effect of Nanoparticle Ligand Charge on Protein Structure," Langmuir 2005, 21, 12080-12084
Brown et al., "Interaction between nanoparticles and cytokine proteins: impact on protein and particle functionality," Nanotechnology 21 (2010) 215104 (9pp).
Saptarshi et al., "Interaction of nanoparticles with proteins: relation to bio-reactivity of the nanoparticle," Journal of Nanobiotechnology 2013, 11:26, 1-12.
Le Bon et al (2001), Immunity, vol. 14, pp. 461-470.
Lin et al (2009) Biomaterials, 30(19), pp. 3332-3342.
Adler, E.M., "Specialy delivery to the lymph node," Science Signaling (2009) 2:ec352.
Agnihotri, S.A. et al., "Recent advances on chitosan-based micro- and nanoparticles in drug delivery," J. Control. Release (2004) 100:5-28.
Combadiere, B. et al., "Particle-based vaccines for transcutaneous vaccination," Comparative Immun. Microbiol. Infect. Diseases (2008) 31:293-315
Cui, Z. et al., "Chitosan-based nanoparticles as potential oral delivery systems of proteins and vaccines: a mechanistic approach," J. Control. Rel. (2001) 75:409-419.
Des Rieux, A. et al., "Nanoparticules as potential oral delivery systems of proteins and vaccines: a mechanistic approach," J. Control. Rel. (2006) 116:1-27.
Hans, M.L. et al., "Biodegradable nanoparticles for drug delivery and targeting," Curr. Opin. In Solid State and Materials Science (2002) 6:319-327.

(Continued)

*Primary Examiner* — Prema Mertz
(74) *Attorney, Agent, or Firm* — Michael Best & Friedrich LLP

(57) ABSTRACT

Provided are nanoparticles comprising heparin, chitosan, and at least one immunomodulatory agent, e.g. a cytokine. The cytokine can be selected from the group consisting of TNF, IL-12, IL-2, IL-23, IL-1α, IL-10, IL-18, and combinations thereof. Further provided are methods of making a nanoparticle comprising mixing a first composition comprising heparin with a second composition comprising chitosan in the presence of at least one cytokine to form a third composition. Further provided are methods of modulating an immune response comprising co-administering to a subject an antigen or vaccine with nanoparticles comprising heparin, chitosan, and at least one cytokine.

5 Claims, 26 Drawing Sheets

(56) References Cited

OTHER PUBLICATIONS

Kemp, M.M. et al., "Heparin-based nanoparticles," Nanomedicine and Nanobiotechnology (2010) 2:77-87.
Koping-Hoggard, M. et al., "Nanoparticles as carriers for nasal vaccine delivery," Exp. Rev. in Vaccines (2005) 4:185-196.
Kunder, C.A. et al., "Mast cell-derived particles deliver peripheral signals to remote lymph notes," J. Exp. Med. (2009) 206:2455-2467.
Lamprecht, A. et al., "Biodegradable nanoparticles for targeted drug delivery in treatment of inflammatory bowel disease," J. Pharm. Exp. Ther. (2001) 299:775-781.
Liu, Z. et al., "Heparin/chitosan nanoparticie carriers prepared by polyelectrolyte complexation," J. Biomed. Mat. Res. Part A (2007) 83A:806-812.
Liu, Z. et al., "Polysaccharide-based nanoparticies as drug delivery systems," Adv. Drug Del. Rev. (2008) 60:1650-1662.
McLachlan, J. B. et al., "Mast cell activators: a new class of highly effective vaccine adjuvants," Nature Med. (2008) 14:536-541.
Rao, D.A. et al,, "Biodegradable PLGA based nanoparticles for sustained regional lymphatic drug delivery," J. Pharm. Sci, (2010) 99:2018-2031
Rao, D.A. et al, "Effect of size and surface properties of biodegradable PLGA-PMA: PLA: PEG nanoparticles on lymphatic uptake and retention in rats." J. Control. Rel. (2008) 132:e45-47.
Reddy, S.T. et al., "In vivo targeting of dendritic cells in lymph nodes with poly(propylene sulfide) nanoparticles," J. Control. Rel. (2006) 112:26-34.
Sosnik, A. et al., "Polymeric nanocarriers: new endeavors for the optimization of the technological aspects of drugs," Recent Patents on Biomedical Engineering (2008) 1:43-59.
Zaharoff, D.A. et al., "Chitosan solution enhances both humoral and cell-mediated immune responses to subcutaneous vaccination," Vaccine (2007) 25:2085-2094.

\* cited by examiner

SEQUENCE LISTING

```
<160> NUMBER OF SEQ ID NOS: 2

<210> SEQ ID NO 1
<211> LENGTH: 32
<212> TYPE: DNA
<213> ORGANISM: Artificial sequence
<220> FEATURE:
<223> OTHER INFORMATION: tnf forward primer

<400> SEQUENCE: 1
gatctcgaga tgagcacaga aagcatgatc cg                                    32
```

```
<210> SEQ ID NO 2
<211> LENGTH: 33
<212> TYPE: DNA
<213> ORGANISM: Artificial sequence
<220> FEATURE:
<223> OTHER INFORMATION: tnf reverse primer

<400> SEQUENCE: 2
ggtggatccc gcagagcaat gactccaaag tag                                33
```

METHOD OF TREATING FOOD ALLERGIES BY ADMINISTERING A NANOPARTICLE COMPRISING HEPARIN AND CHITOSAN ENCAPSULATING IL-12

CROSS-REFERENCE TO RELATED APPLICATIONS

This application is a divisional of and claims priority to U.S. patent application Ser. No. 13/252,516, filed Oct. 4, 2011, which claims the benefit of U.S. Provisional Patent Application No. 61/389,457, filed Oct. 4, 2010, and are incorporated herein by reference in their entireties.

STATEMENT REGARDING FEDERALLY SPONSORED RESEARCH

This invention was made with government support under federal grant number R21 DK 077307-01 from the NIH. The U.S. Government has certain rights to this invention.

FIELD OF INVENTION

The disclosure relates to compositions, methods of making compositions, and methods for delivery of active agents including cytokines. Moreover, the disclosure provides adjuvant compositions for vaccines to modulate (e.g., inhibit or enhance) cellular responses, such as an immune response.

INTRODUCTION

While vaccines for many childhood diseases have resulted in plummeting mortality rates in the human population over the last century, significant challenges remain for which current vaccine formulations fall short. Influenza (flu) is one highly contagious disease with unique epidemiological and clinical obstacles that are not adequately addressed by current vaccination strategies. Some deficiencies include the inability to protect the entire population because of limited efficacy of vaccination in certain populations, such as the elderly who are not always immuno-responsive, and the difficulty of producing large amounts of strain-specific flu antigens quickly enough to vaccinate the world population in the face of a spreading pandemic strain. As a consequence of these limitations, an appreciable population remains highly susceptible to a pandemic strain, even after immunization.

Adjuvants are compounds that are incorporated into vaccine formulations to boost immune responses, but even with adjuvants, the resulting immune responses are still often suboptimal. Because most have inherent toxicity, safe adjuvants have been difficult to identify. Currently employed adjuvants typically work by activating dendritic cells (DCs) at the site of vaccine administration and enhancing the trafficking of antigen-loaded DCs to the draining lymph nodes (DLNs) where antigen presentation to T cells occurs.

The draining lymph nodes (DLNs) are dynamic lymphoid structures that coordinate the development of specific immune responses after microbial or vaccine challenge. In response to these peripheral events, the DLN quickly undergoes significant structural changes, including rapid growth and vascular remodeling. This enlargement, which is largely attributable to enhanced recruitment and retention of naive lymphocytes from the circulation, increases the probability that rare lymphocytes bearing relevant specificities will be present to interact with activated tissue-derived antigen presenting cells (APCs), which migrate from inflamed tissues via afferent lymphatic vessels. This interaction between lymphocytes and APCs occurring within DLNs is the initiating event in the development of the adaptive immune response.

Accordingly, there is a need for additional and improved compositions that have adjuvant activity, as well as vaccines and methods for enhancing immune responses that include such adjuvant compositions.

SUMMARY

In an aspect the disclosure provides a nanoparticle comprising heparin, chitosan, and at least one immunomodulatory agent, such as a cytokine. In embodiments, the heparin and chitosan may not be cross-linked. In embodiments, the cytokine comprises TNF, IL-12, IL-1α, IL-18, IL-2, IL-23, IL-10, IFN, or any other cytokine, chemokine, or immunomodulatory agent, and any combination thereof. In some embodiments, the nanoparticle can further comprise an antigen. In some embodiments, the antigen comprises ovalbumin.

In an aspect the disclosure provides a method of making a nanoparticle comprising mixing in the presence of at least one immunomodulatory agent (e.g., a cytokine) a first composition comprising heparin, together with a second composition comprising chitosan, to form a third composition comprising the nanoparticle. Embodiments can further comprise any one or combination of adjusting the pH of the third composition to neutrality; centrifuging the third composition to form a pellet; and washing the pellet.

In an aspect the disclosure provides a method of modulating an immune response in a subject, comprising co-administering to the subject an antigen or vaccine and nanoparticles comprising heparin, chitosan, and at least one immunomodulatory agent, such as a cytokine. In various embodiments the method can provide for an enhanced immune response, a polarized immune response, or a suppressed immune response.

In another aspect the disclosure provides a method of treating a disease, disorder, or a condition associated with a disease or disorder comprising administering to a subject in need of treatment a nanoparticle comprising heparin, chitosan, and at least one immunomodulatory agent. In embodiments the at least one immunomodulatory agent comprises a cytokine selected from the group consisting of TNF, IL-12, IL-2, IL-23, IL-1α, IL-18, and IFN.

Aspects of the disclosure relate to a composition comprising the nanoparticle described herein and a vehicle or carrier.

Further aspects of the disclosure relate to a vaccine comprising the nanoparticle described herein, an immunogen, and an optional pharmaceutically acceptable vehicle or carriers.

An aspect of the disclosure relates to an adjuvant composition comprising the nanoparticle described herein and an optional vehicle or carrier.

Other aspects and embodiments of the disclosure will become apparent by consideration of the detailed description and accompanying drawings.

BRIEF DESCRIPTION OF THE DRAWINGS

FIG. 23D is a graph of the percent antibody bound after stringent washing. FIG. 23E is a graph showing survival of mice vaccinated as in (A)-(B) and challenged with H1N1 Flu.

DETAILED DESCRIPTION

Figure 1:
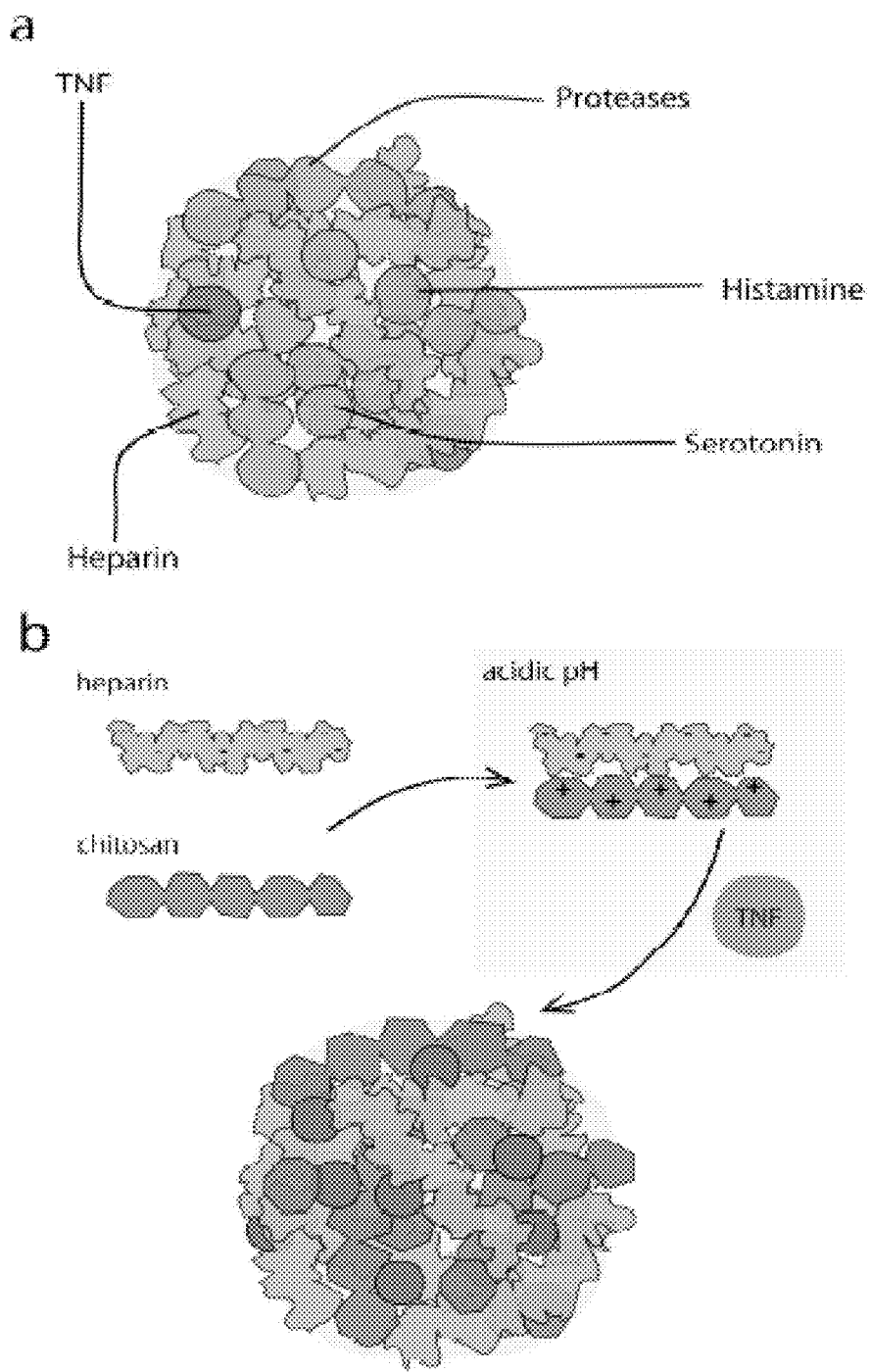
FIG. 1A is a schematic diagram of a mast cell (MC) granule containing mediators, held within a matrix of carbohydrates and proteins.
FIG. 1B is a schematic diagram of a nanoparticle made with a similar matrix with chitosan, positively charged under acidic conditions, and heparin.

Before describing any aspects and embodiments, it is to be understood that the claims are not limited to the details of construction and the arrangement of components set forth in the following description or illustrated in the drawings.

During infection, signals from the periphery are known to reach draining lymph nodes (DLNs), but how these molecules, such as inflammatory cytokines, traverse the significant distances involved without dilution or degradation was unclear. As shown in the Examples, peripheral mast cells (MCs), upon activation, release stable submicrometer heparin-based particles containing tumor necrosis factor and other proteins. These complexes enter lymphatic vessels and rapidly traffic to the DLNs. This physiological drug delivery system facilitates communication between peripheral sites of inflammation and remote secondary lymphoid tissues.

As described herein, including the Examples, a form of extracellular inflammatory communication exists over long distances, and MC-derived particles can deliver signals from the periphery to the LNs. Activation of dendritic cells (DCs) plays a role in the initiating events in the adaptive immune response. However, the trafficking of these cells to the draining lymph nodes (DLN), their subsequent interactions with DLN lymphocytes, and the activation and interactions of lymphocytes themselves also play a role in the amplification of the adaptive immune response and the formation of protective immunological memory during infection. Optimal immune responses are produced due to rapid communication between the periphery and the DLN during natural infection, in part through the actions of MCs, which can influence DC migration and the inflammatory milieu of the DLN, resulting in heightened antibody responses. It has long been recognized that MCs release stable particles in response to various stimuli, including pathogens, and as shown in the Examples, these particles retain inflammatory mediators and travel with them to the DLNs. These traveling nanoparticles drastically reorganize DLNs, being responsible in the host for the initial swelling that occurs during bacterial infection, where DLNs double in size. It is likely that the targeting of products to DLNs also contributes to other processes that are known to be influenced by MCs, including the development of high affinity antibodies. Functional analysis of natural MC-derived particles revealed that associated TNF, specifically, is responsible for these changes, likely through the slow release of this cytokine. Cytokines, themselves, can be used as effective adjuvants, although significant quantities of mediators are required to achieve observable effects. Exocytosed MC granules, therefore, act as physiological drug delivery devices, ensuring that minute quantities of pro-inflammatory mediators are efficiently delivered directly to the DLNs, in a form protected from degradation and dilution, in order to modulate an immune response (e.g., promote the adaptive immune process or inhibit autoimmune process).

The mast cell strategy may be harnessed to optimize immunity through targeted delivery of mediator-containing particles. Natural MC particles consist primarily of carbohydrate, heparin, and proteases and are formed by the process of polyelectrolyte complexation at the cellular level, where sub-micron sized structures are held together based on charged interactions (FIG. 1). In a general sense, the disclosure provides nanoparticles that functionally replicate the efficient lymph node targeting of MC-derived particles. The engineered particles comprise heparin and chitosan (a non-immunogenic carbohydrate, which may be derived from crustacean shells). As discussed herein chitosan provides technical advantages over other positively charged compounds. Targeted delivery of an immunomodulatory agent (e.g., cytokines) in heparin-chitosan complexes can recapitulate the adjuvant activity of natural MC activation during infection in vivo and provide a new class of adjuvant that addresses the limitations of the current vaccine technology (e.g., influenza vaccine) and serves as a basis for optimizing existing vaccine formulations.

In an aspect, the disclosure provides a nanoparticle comprising heparin, chitosan, and at least one immunomodulatory agent. As used herein, "immunomodulatory agent" refers to a substance that can induce an effect on the immune system, e.g., an immunosuppressor, an immunostimulator, etc. In certain embodiments, immunomodulatory agent comprises a pro-inflammatory mediator. In certain embodiments, immunomodulatory agent comprises a cytokine. The ratio of heparin and chitosan in the nanoparticle can be varied and adjusted to provide for desired physical characteristics of the nanoparticle (e.g., size such as volume, surface area, surface charge, stability, etc.). In embodiments the ratio of heparin to chitosan can be from about 2:1, about 1.5:1, about 1:1, about 1:1.5, or about 1:2. The relative mass ratio of heparin to chitosan may be about 0.2 to about 5. In alternative embodiments, the nanoparticles comprise heparin, PGLA, and at least one immunomodulatory agent, wherein the molar ratio of GA/LA in the polymer may be about 0.2 to about 5, with a molecular weight range of about 15,000 to about 200,000. The particles may be biocompatible. The particles may be biodegradable. In certain embodiments, the particles are not chemically cross-linked. The particles may be about 50 nm to about 10 µm in diameter, or about 150 nm to about 5 µm in diameter.

Cytokines can include any cytokine known in the art such as, for example, lymphokines, interleukins, and chemokines (e.g., agents that can induce directed chemotaxis in responsive cells). In certain embodiments, cytokines comprise a pro-inflammatory cytokine. Certain non-limiting examples of cytokines include TNF, IL-2, IL-23, IL-12, IL-1α, IL-18, IL-10, IFN as well as C, CC, CxC, or $CX_3C$ family of chemokines and combinations thereof. In certain embodiments, nanoparticles comprise TNF. In certain embodiments, the nanoparticles comprise IL-12. In certain embodiments, the nanoparticles comprise IL-10. Further provided are compositions comprising nanoparticles. The compositions may comprise the heparin-chitosan nanoparticles disclosed herein, wherein the nanoparticles comprises a cytokine or a combination of different cytokines or chemokines. In embodiments, the compositions may comprise a mixture of nanoparticles, each comprising a different cytokine.

In certain embodiments, the nanoparticles may further comprise an antigen or immunogen. As used herein, the term "immunogen" or "antigen" refers to any substance or organism that provokes an immune response (produces immunity) when introduced into the body. In some embodiments, the antigen may be derived from an infectious agent or any other agent that a vaccine is directed against. The particular immunogen used (e.g., proteins, peptides, polysaccharides, lipids, and the like, including glycoproteins, glycolipids, glycoproteins, lipoproteins, lipopolysaccharides and the like) is not critical to the invention. Immunogens are known in the art and can be incorporated for use in the methods and compositions provided herein using any common method. Non-limiting lists of suitable immunogens for use in the various aspects and embodiments described herein can be found in the literature, for example, BioCarb Chemicals Catalogue; and The Jordan Report: Accelerated Development of Vaccine 1995 NIH, Bethesda, Md., 1995, both of which are incorporated herein by reference.

Antigens or immunogens may include, but are not limited to, microbial antigens such as parasitic antigens, viral antigens, bacterial antigens, fungal antigens, cancer antigens, vaccine antigen additive drugs such as cocaine and nicotine derivatives, attenuated or killed bacteria, attenuated or killed virus, autoimmune antigens, or nonstructural protein antigens, and any combination thereof. In some embodiments, the antigen comprises at least one flu, autoimmune, cocaine, or cancer antigen.

In some embodiments an immunogen comprises any immunogen derived from bacterial surface polysaccharides which can be used in carbohydrate-based vaccines. Bacteria typically express carbohydrates on the cell surface as part of glycoproteins, glycoplipids, O-specific side chains of lipopolysaccharides, capsular polysaccharides and the like. Non-limiting examples of suitable bacterial strains include *Streptococcus pneumonia, Neisseria meningitidis, Haemophilus influenza, Klebsiella* spp., *Pseudomonas* spp., *Salmonella* spp., *Shigella* spp., and Group B streptococci. In some embodiments any known bacterial carbohydrate epitope (e.g., those described in Sanders, et al. *Pediatr. Res.* 1995, 37, 812-819; Bartoloni, et al. *Vaccine* 1995, 13, 463-470; Pirofski, et al., *Infect. Immun.* 1995, 63, 2906-2911; U.S. Pat. No. 6,413,935; and International Publication No. WO 93/21948) can be used as an immunogen in the compositions and methods herein described.

Some embodiments provide for an immunogen that comprises a viral antigen. Non-limiting examples of viral antigens or viral immunogens include those derived from HIV (e.g., gp120, nef, tat, pol), influenza, and West Nile Virus (WNV). In some embodiments, the antigen can comprise whole killed virus or attenuated virus.

Some embodiments provide for an immunogen that comprises a fungal antigen. Non-limiting examples of fungal antigens include those derived from *Candida albicans, Cryptococcus neoformans, Coccidioides* spp., *Histoplasma* spp., and *Aspergillus* spp.

Some embodiments provide for an immunogen that comprises an antigen derived from a parasite. Non-limiting examples of parasitic antigens include those derived from *Plasmodium* spp., *Trypanosoma* spp., *Schistosoma* spp., *Leishmania* spp. and the like.

In some embodiments the immunogen comprises a carbohydrate epitope. Non-limiting examples of carbohydrate epitopes that can be used in the aspects and embodiments described herein include: Galα1,4Galβ (for bacterial vaccines); GalNAcα (for cancer vaccines); Manβ1,2(Manβ)$_n$ Manβ-(for fungal vaccines useful against, for example, *C. albicans*), wherein n is any integer, including zero; GalNAcβ1,4(NeuAcα2,3)Galβ1,4Glcβ-O-ceramide (for cancer vaccines); Galα1,2(Tyvα1,3)Manα1,4Rhaα1, 3Galα1,2-(Tyα1,3)Manα4Rha- and Galα1,2(Abeα1,3) Manα1,4Rhaα1,3Galα1,2(Abeα1,3) Manα1,4Rhaα1, 3Galα1,2(Abeα1,3)Manα1,4Rha (both of which are useful against, for example, *Salmonella* spp.). Description of other exemplary carbohydrate epitopes as antigens or immunogens and the synthesis thereof are described further in U.S. Pat. No. 6,413,935, incorporated herein by reference.

In some embodiments, the immunogen can be an anthrax immunogen; i.e. an immunogen that produces protective immunity to *Bacillus anthracis*, such as anthrax vaccine, A, (see, e.g., U.S. Pat. No. 5,728,385; BioThrax® Emergent Biosolutions, Rockville, Md.). Other examples of immunogens or antigens include, but are not limited to, those that produce an immune response or antigenic response to the following diseases and disease-causing agents: adenoviruses; *Bordetella pertussus*; Botulism; bovine rhinotracheitis; *Branhamella catarrhalis*; canine hepatitis; canine distemper; Chlamydiae; Cholera; coccidiomycosis; cowpox; cytomegalovirus; cytomegalovirus; Dengue fever; dengue toxoplasmosis; Diphtheria; encephalitis; Enterotoxigenic *Escherichia coli*; Epstein Barr virus; equine encephalitis; equine infectious anemia; equine influenza; equine pneumonia; equine rhinovirus; feline leukemia; flavivirus; Globulin; *Haemophilus* influenza type b; *Haemophilus influenzae; Haemophilus pertussis; Helicobacter pylori; Hemophilus* spp.; hepatitis; hepatitis A; hepatitis B; Hepatitis C; herpes viruses; HIV; HIV-1 viruses; HIV-2 viruses; HTLV; Influenza; Japanese encephalitis; *Klebsiellae* spp. *Legionella pneumophila; leishmania*; leprosy; lyme disease; malaria immunogen; measles; meningitis; meningococcal; Meningococcal Polysaccharide Group A, Meningococcal Polysaccharide Group C; mumps; Mumps Virus; mycobacteria; *Mycobacterium tuberculosis; Neisseria* spp; *Neisseria gonorrhoeae; Neisseria meningitidis*; ovine blue tongue; ovine encephalitis; papilloma; parainfluenza; paramyxovirus; paramyxoviruses; Pertussis; Plague; *Pneumococcus* spp.; *Pneumocystis carinii*; Pneumonia; Poliovirus; *Proteus* species; *Pseudomonas aeruginosa*; rabies; respiratory syncytial virus; rotavirus; *Rubella*; Salmonellae; schistosomiasis; Shigellae; simian immunodeficiency virus; Smallpox; *Staphylococcus aureus; Staphylococcus* spp.; *Streptococcus pneumoniae; Streptococcus pyogenes; Streptococcus* spp.; swine influenza; tetanus; *Treponema pallidum*; Typhoid; Vaccinia; varicella-zoster virus; and *Vibrio cholerae*. The antigens or immunogens can include various toxoids, viral antigens and/or bacterial antigens such as antigens commonly employed in the following vaccines: chickenpox vaccine; diphtheria, tetanus, and pertussis vaccines; *haemophilus influenzae* type b vaccine (Hib); hepatitis A vaccine; hepatitis B vaccine; influenza vaccine; measles, mumps, and rubella vaccines (MMR); pneumococcal vaccine; polio vaccines; rotavirus vaccine; anthrax vaccines; and tetanus and diphtheria vaccine (Td) (see, e.g., U.S. Pat. No. 6,309,633).

In some embodiments, antigens or immunogens can include any type of antigen associated with cancer such as, for example, tumor associated antigens (TSAs) (including antigens associated with leukemias and lymphomas) such as carcinoembryonic antigen, prostatic acid phosphatase, and antigens that are associated with agents that can cause cancer (e.g., tumorigenic viruses such as, for example, adenovirus, HBV, HCV, HTLV, Kaposi's sarcoma-associated herpes virus, HPV (Gardasil®), and the like).

Antigens or immunogens that are used to carry out the present invention include those that are derivatized or modified in some way, such as by conjugating or coupling one or more additional groups thereto to enhance function or achieve additional functions such as targeting or enhanced delivery thereof, including techniques known in the art such as, for example, those described in U.S. Pat. No. 6,493,402 to Pizzo et al. (α-2 macroglobulin complexes); U.S. Pat. No. 6,309,633; U.S. Pat. No. 6,207,157; and U.S. Pat. No. 5,908,629.

Certain embodiments provide for nanoparticles that are prepared for administration to a subject by mixing the nanoparticle at the desired degree of purity with one or more physiologically acceptable carriers, i.e. carriers that are nontoxic to recipients at the dosages and concentrations employed, or any additional known adjuvant. In some embodiments, an additional adjuvant is incorporated with an immunogen, as described herein, and the immunomodulatory agent(s) in the nanoparticle. In embodiments, the additional adjuvants and carriers share no immune epitopes with the immunogen/target antigen, but can provide further stimulation of the immune response to the immunogen/target antigen. Suitably, this formulation comprises combining one or more buffers, low molecular weight polypeptides, proteins, amino acids, carbohydrates including glucose or dextrans, chelating agents such as EDTA, and other excipients. While a carrier can act as an adjuvant, carriers can generally distinguished from adjuvants in that carriers comprise water insoluble macromolecular particulate structures which aggregate the antigen. Typical carriers may include aluminum hydroxide, latex particles, bentonite, and liposomes. Saponin derivatives are also suitable adjuvants.

In some embodiments the administration is via injection (e.g., intramuscular or subcutaneous), intravenous delivery, mucosal delivery, intranasal delivery, inhalation delivery, or delivery through catheter or other surgical tubing can be used. Alternative routes include tablets and the like, commercially available nebulizers for liquid formulations, and inhalation of lyophilized or aerosolized nanoparticles. Liquid formulations may be utilized after reconstitution from powdered or freeze-dried nanoparticle formulations.

The nanoparticles described herein can also be administered via other microparticulate delivery systems or sustained release formulations placed in certain tissues including blood and the lymphocytic system. Non-limiting examples of sustained release carriers include semipermeable polymer matrices in the form of shaped articles, e.g. suppositories, or microcapsules. Implantable or microcapsular sustained release matrices include polylactides (U.S. Pat. No. 3,773,919 and EP 58,481) copolymers of L-glutamic acid and gamma ethyl-L-glutamate (U. Sidman et al., *Biopolymers* 1985, 22, 547-556), poly(2-hydroxyethyl-methacrylate) or ethylene vinyl acetate (R. Langer et al., *J. Biomed. Mater. Res.* 1981, 15, 167-277; and R. Langer, *Chem. Tech.* 1982, 12, 98-105). Embodiments provide carriers that include pharmaceutically acceptable polymers, such as collagen, polylysine, polylactic acid, polymethylacrylate, polyurethane, polyglycolic acid, hydroxypropylcellulose, agar and agarose. Methods for preparing these polymers in cross-linked and/or gel form are well known, and the methods can be readily adapted to incorporate the nanoparticles herein described. Many of the polymers, such as agar, collagen, and polyurethanes can be formulated in permeable cross-linked structures which can allow for nanoparticle movement within and out of the matrices at a selected rate.

Further provided are methods of making a nanoparticle. Advantageously, the methods described herein and the nanoparticles generated using the methods do not require cross-linking of the chitosan and/or heparin molecules in order to form stable particles. In some embodiments, however, optional cross-linking agents such as those known in the art can be used to provide additional stability to the nanoparticles and compositions comprising the nanoparticles. Methods may comprise mixing in the presence of at least one cytokine a first composition comprising heparin, together with a second composition comprising chitosan, to form a third composition comprising the nanoparticle. In some embodiments, the cytokine can be included in either the first composition or the second composition. In some embodiments, a separate composition comprises the cytokine, and the separate composition is added to the first and second compositions. Without being limited to mechanism, it may be that mixing the first and second compositions in the presence of at least one cytokine may entrap the cytokine within the particle structure. Mixing may comprise vortexing. In some embodiments, the compositions are mixed in the presence of at least one antigen, as described above.

In some embodiments the methods may further comprise subsequently adjusting the pH of the third composition to neutrality. The pH can be adjusted using any pH adjusting agent known in the art including, for example, buffer solutions, weak or strong acids and/or bases, and the like. In some embodiments the methods provide for centrifuging the third composition to form a pellet. Some embodiments of the methods provide for washing the pellet. Some embodiments of the invention provide for filtering or selecting by methods known in the art for selecting particle size. Some embodiments of the methods provide for concentrating the particles. In some embodiments, the method provides for any or all of adjusting the pH, centrifuging to form a pellet, and/or washing the pellet.

As mentioned previously, heparin has a very high negative charge density. Chitosan, in contrast, is a polycation at pH <5.5 because of protonation of the amino groups in the side chains of the polysaccharide. When solutions containing these compounds are mixed, they can rapidly phase separate to form spherical particles because of electrostatic interaction of the oppositely charged heparin and chitosan. Since chitosan becomes protonated at acidic pH, giving it a positive charge, modulation of the pH can influence the extent of complexation, control the size of aggregates, and ensure the stability of particles when the solution is returned to normal pH. Optimization of pH can result in stable particles of relatively uniform size that closely approximate the size of purified MC-derived particles. In embodiments, the method provides for mixing the first and second compositions at an acidic pH. In some embodiments, the first and second compositions may be mixed at a pH of about 3 to about 6, about 4 to about 5, or about 4.5. The pH of the third composition may be acidic. The pH of the third composition may be a pH of about 3 to about 6, about 4 to about 5, or about 4.5. The particles may be formed by mixing solutions of varying salt concentrations from solutions in water to solutions in saline. The first and second compositions may be mixed at room temperature. The first and second compositions may be mixed by a suitable means known in the art including, but not limited to, vortexing (e.g., for less than about 60 sec) or magnetic stirring (e.g., at about 400-800 rpm for up to about 10 min). Particles may be stored at any suitable temperature including about −20° C. to about 25° C., about 0° C. to about 10° C., or about 4° C.

The heparin and chitosan may be mixed at a ratio of about 2:1, about 1.5:1, about 1:1, about 1:1.5, or about 1:2 with each other. The heparin and chitosan may be mixed at a ratio of about 1:1 with each other. The first and second compositions may each independently be solutions including, but not limited to, water, PBS (pH 7.4 and 0.1 M), or other suitable solution. The heparin may present in the first composition in an amount of at least about 0.01%, at least about 0.1%, at least about 0.5%, or at least about 1%. The heparin may present in the first composition in an amount of less than about 8%, less than about 5%, less than about 3%, less than about 2%, or less than about 1%. The chitosan may be present in the second composition in an amount of at least about 0.01%, at least about 0.1%, at least about 0.5%, or at least about 1%. The chitosan may be present in the second composition in an amount of less than about 8%, less than about 5%, less than about 3%, less than about 2%, or less than about 1%. The heparin and chitosan may be present in the nanoparticle at a ratio of about 2:1, about 1.5:1, about 1:1, about 1:1.5, or about 1:2 with each other. Embodiments provide for the content of heparin and chitosan comprising the nanoparticle at a ratio of about 1:1 with each other.

As mentioned above, currently employed adjuvants typically work by activating dendritic cells (DCs) at the site of vaccine administration and enhancing the trafficking of antigen-loaded DCs to the DLNs where antigen presentation to T cells occurs. Without being limited to any mechanism, use of the nanoparticles described herein may bypass the limitation of acting largely at the site of vaccine administration, through direct targeting of an adjuvant to the DLNs. As illustrated in the Examples, the nanoparticles described herein, when injected, can move to the DLN and effect functional changes, including promoting lymph node hypertrophy, inducing germinal center formation, or enhancing T cell production of IFN-γ. The nanoparticles may mimic mast cell (MC) granules and travel from the site of administration at the periphery directly to draining lymph nodes to promote an adaptive immune response.

In an aspect, the disclosure provides a composition including the nanoparticles described herein, wherein the composition is formulated as an adjuvant.

In a further aspect, the disclosure provides methods of modulating an immune response in a subject. The methods may comprise administering to the subject the nanoparticles as described herein in an amount effective to modulate the immune response. In some embodiments, the nanoparticle increases the amount of IgA, IgG1, IgG2, or a combination thereof in the subject. In some embodiments, administration of the nanoparticle increases the amounts of both IgG1 and IgG2 in the subject.

As detailed above, modulating an immune response can include increasing (enhancing) and polarizing (e.g., inducing the response toward either a Th1 or Th2 profile) an immune response. In an aspect, the disclosure provides methods of enhancing or polarizing an immune response. The nanoparticle may comprise at least one of TNF, IL-2, IL-12, IL-23, IL-1α, IL-18, and IFN, or any combination thereof as well as additional cytokines and/or chemokines In some embodiments, the nanoparticle comprises at least one of TNF and IL-12. In some embodiments, the nanoparticle further comprises or may be co-administered with a vaccine. The methods may comprise co-administering a vaccine with the nanoparticles described above. An effective amount of nanoparticles and vaccine may be co-administered to a subject in need thereof. The nanoparticles may affect the developing adaptive immune response. The nanoparticles may be co-administered with a vaccine to improve the quality and magnitude of the immune response to the vaccine. Co-administration of the nanoparticles with a vaccine may result in greater antibody titers or cell mediated immune responses to the vaccine antigen relative to the titers or immune responses without the nanoparticles. The selected cytokines of the nanoparticles may enable the fine-tuning of the character of the developing adaptive immune response. The nanoparticles may be tailored to elicit an optimal immune response for each vaccine to be most effective for protection.

In some embodiments, the method can boost an immune response in a subject whose immune system is impaired such as, for example, when the subject is immunocompromised or immunodeficient or non-responsive. Immunocompromised or non-responsive subjects include, but are not limited to, the elderly, those with an autoimmune disease, those that are pregnant, those with HIV or AIDS, those undergoing chemotherapy or radiation therapy for cancer, those having an immunodeficiency syndrome, or those having an immune system impaired by age, genetic disorder, environmental toxins, disease, or a therapy.

Thus, some embodiments provide methods of attenuating or decreasing an immune response in a subject. In such embodiments, the nanoparticle can comprise an immunosuppressive agent such as, for example, IL-10 or TGFβ. In some embodiments, the nanoparticle further comprises or may be co-administered with one or more autoimmune antigens. In some embodiments, the subject has a condition or disorder associated with an autoimmune disease. As is known in the art, an autoimmune disease is a disease or disorder arising from an overactive immune response of the body against substances or tissues normally present in the body. Autoimmune diseases include, but are not limited to, rheumatoid arthritis, lupis, multiple sclerosis, celiac disease, Crohn's disease, diabetes mellitus type 1, and the like.

In a further aspect, provided are methods of enhancing an immune response for therapeutic purposes. In embodiments, the aspect comprises co-administering to an infected or diseased subject a vaccine with a nanoparticle as described herein to reduce symptoms, morbidity and/or to accelerate recovery. The nanoparticle may comprise or may be co-administered with the vaccine. In some embodiments, the nanoparticle comprises at least one immunomodulatory agent comprising a cytokine. In some embodiments, the cytokine selected may include from the group consisting of TNF, IL-2, IL-12, IL-23, IL-1α, IL-18, and IFN. Further embodiments provide adjuvant compositions comprising a nanoparticle as described herein and a vehicle or carrier that find use, for example in therapeutic and/or prophylactic methods.

In another aspect the disclosure provides a method of treating a disease, disorder, or a condition associated with a disease or disorder comprising administering to a subject in need of treatment a nanoparticle comprising heparin, chitosan, and at least one immunomodulatory agent. In embodiments the at least one immunomodulatory agent comprises a cytokine selected from the group consisting of TNF, IL-12, IL-2, IL-23, IL-1α, IL-18, and IFN. The disease, disorder, or a condition associated with a disease or disorder can be diagnosed or identified in the subject (e.g., a mammal such as a human) using any suitable technique available to the practitioner (e.g., medical personnel, clinician, lab technician, etc.). In some embodiments the disease or disorder, or the associated condition is responsive to immune-based therapy such as, for example, therapy comprising administration of a cytokine (e.g., TNF, IL-12, IL-2, IL-23, IL-1α, IL-18, and IFN). In some embodiments the disease or disorder, or the associated condition is treatable with another suitable active agent for the disease or disorder (e.g., antiviral, chemotherapeutic, radiation therapy, etc.) and the treatment is enhanced by an adjuvant or co-therapy comprising administration of the nanoparticle compositions disclosed herein.

In a further aspect, provided are methods for treating a chronic viral infection comprising administering to a subject a nanoparticle as described herein. In some embodiments, the nanoparticle comprises IFN. In embodiments, the subject is diagnosed with a viral infection. In some embodiments, the subject exhibits one or more clinical indications of a viral infection.

In a further aspect, provided are methods of attenuating an immune response comprising co-administering to a subject a vaccine with a nanoparticle as described herein. The nanoparticle may comprise or may be co-administered with the vaccine. In some embodiments, the nanoparticle comprises at least one immunosuppressive agent. In some embodiments, the nanoparticle comprises IL-10.

In a further aspect, provided are methods of treating an allergic condition including food allergies and asthma, comprising administering to a subject in need of treatment a nanoparticle as described herein. In some embodiments, the nanoparticle comprises IL-10 alone or in combination with an antigen.

In a further aspect, provided are methods of treating an autoimmune disease comprising administering to a subject in need of treatment a nanoparticle as described herein. Further provided is a composition for treating an autoimmune disease comprising a nanoparticle as described herein. In some embodiments of these aspects, the nanoparticle comprises IL-10.

In a further aspect, provided are prophylactic compositions comprising a nanoparticle as described herein. In some embodiments, the nanoparticle comprises IL-10. In some embodiments, the nanoparticle further comprises an autoimmune disease antigen. The composition may decrease the likelihood of developing an autoimmune disease in the subject.

In a further aspect, provided are methods for preventing the severity or occurrence of a disease or disorder in a subject, the methods comprising administering to a subject in need thereof a nanoparticle as described herein. In some embodiments, the nanoparticle comprises IL-10. In some embodiments, the nanoparticle further comprises an autoimmune disease antigen.

The nanoparticles may be co-administered with any vaccine known in the art, such as a prophylactic or a therapeutic vaccine, including but not limited to, a flu vaccine. Flu may include viruses including, but not limited to, severe acute respiratory syndrome, avian influenza, H1N1 influenza, seasonal influenza, and others as listed above.

In some embodiments of the aspects described herein, the nanoparticles can be formulated to release an active agent, such as a cytokine. In some embodiments, the release can be a delayed release (e.g., released over a period of time). In some embodiments, the agent may be released over the course of at least about 1 min, at least about 5 min, at least about 10 min, at least about 30 min, at least about 1 h, at least about 2 h, at least about 4 h, at least about 6 h, at least about 12 h, at least about 18 h, at least about 24 h, at least about 36 h, at least about 48 h, at least about 1 week, at least about 2 weeks, at least about 3 weeks, or at least about 4 weeks. In some embodiments, the cytokine may be release over the course of less than about 4 weeks, less than about 3 weeks, less than about 2 weeks, less than about 1 week, less than about 48 h, less than about 36 h, less than about 24 h, less than about 18 h, less than about 12 h, less than about 6 h, less than about 4 h, less than about 2 h, less than about 1 h, or less than about 30 min.

"Administration" or "administering" refers to delivery of the nanoparticles by any appropriate route to achieve the desired effect. Administration may include, but is not limited to, oral, sublingual, intramuscular, subcutaneous, intravenous, transdermal, topical, parenteral, buccal, rectal, mucosal, intranasal, and via injection, inhalation, and implants. "Co-administer" refers to simultaneous or sequential administration that is close in time. A particle or composition may be administered before, concurrently with, or after administration of another particle or composition. Nanoparticles may be administered to any subject in need thereof, including subjects who are less immuno-responsive to standard vaccine formulations.

"Effective amount" refers to a dosage of the particles or compositions effective for eliciting a desired effect, commensurate with a reasonable benefit/risk ratio. This term as used herein may also refer to an amount effective at bringing about a desired in vivo effect in an animal, preferably, a human, such as developing an adaptive immune response.

Integrity and bioactivity of released cytokines from the nanoparticles may be evaluated by techniques known by those of skill in the art including, but not limited to, western blot, ELISA, and cell proliferation assays. Physical signs of immune activation in the lymph nodes may be evaluated by techniques known by those of skill in the art including, but not limited to, examination of hypertrophy and development of germinal centers.

It will be understood that any numerical value recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between the lowest value and the highest value enumerated are to be considered to be expressly stated in this application.

Also, it is to be understood that the phraseology and terminology used herein is for the purpose of description and should not be regarded as limiting. The use herein of terms such as "comprising," "including," "having," and variations thereof is meant to encompass the items listed thereafter and equivalents thereof as well as additional items. "Comprising" encompasses the terms "consisting of" and "consisting essentially of." The use of "consisting essentially of" means that the composition or method may include additional ingredients and/or steps, but only if the additional ingredients and/or steps do not materially alter the basic and novel characteristics of the claimed composition or method.

All patents publications and references cited herein are hereby fully incorporated by reference.

While the following examples provide description of certain embodiments, they should be considered merely illustrative and not limiting to the claims.

EXAMPLES

Example 1. Materials and Methods

Animal Studies.

Rat peritoneal MCs were obtained by pooling peritoneal and pleural lavage from Sprague-Dawley rats (Taconic). For compound 48/80 treatment to induce degranulation of mesenteric MCs, rats were injected intraperitoneally with 0.5 mg compound 48/80 in 10 mL PBS.

C57BL/6 mice obtained from NCI were used for most mouse experiments. Single footpad injections were done in a volume of 20 μL of vehicle in most cases. For the LN enlargement experiment, animals were injected on one side with the test substance and with vehicle on the other side to allow for within-animal controls for baseline variations in LN size.

For in vivo tracking studies, 10 μg PMA (Sigma-Aldrich, St. Louis, Mo.) at 1 μg/μL in acetone or acetone alone were applied in two sequential treatments to the footpads of mice anesthetized with pentobarbital. Footpads were allowed to dry completely between applications. DLNs and footpads were harvested after 2 h.

For the isolation of mouse MC-derived particles, peritoneal lavage was performed on two to three mice using DME, and isolated cell suspensions were pooled and stimulated by 1 μM ionomycin (Sigma-Aldrich, St. Louis, Mo.). Treatment with ionomycin was followed by incubation for 15 min in a cell culture incubator, after which the cellular fraction was removed by two rounds of centrifugation at 500 g for 5 min. Exocytosed particles were then pelleted by spinning at 12,000 g for 10 min at 4° C. Particles were washed and resuspended in PBS for injection and quantification using a hemocytometer. Injections were performed with a 10-μL volume. For DLN hypertrophy studies, DLN mass was determined after 24 h as compared with a paired saline control. The saline control for DLN hypertrophy studies using isolated granules contained 5% DME to control for any residual media in the preparation. For tracking studies, $Kit^{W-sh/W-sh}$ mice (Jackson Laboratories, Bar Harbor, Me.) were injected with isolated particles and DLNs were recovered 45 min after particle injection for sectioning and staining with toluidine blue. Images of metachromatic areas were generated using Photoshop (Adobe). All animal experiments were performed according to protocols approved by the Duke University Division of Laboratory Animal Resources and the Duke University Institutional Animal Care and Use Committee.

Cell Culture.

For the generation of TNF-GFP-expressing cells, total RNA was isolated from BMMCs using an RNeasy kit (QIAGEN, Hilden, Germany). Complementary DNA was made using the iScript cDNA synthesis kit (Bio-Rad Laboratories, Weston, Mass.). The tnf gene was PCR amplified using the following primers: tnf forward, 5'-GATCTCGA-GATGAGCACAGAAAGCATGATCCG-3'; (SEQ ID NO:1) and tnf reverse, 5'-GGTGGATCCCGCAGAGCAAT-GACTCCAAAGTAG-3' (SEQ ID NO: 2). The PCR product was digested with XhoI-BamHI, and then ligated with XhoI-BamHI-digested pLEGFP-N1 (BD, Franklin Lakes, N.J.) to generate pTNF-GFP. Sequence accuracy and whether TNF and GFP genes were in frame were confirmed by sequencing. The production of infectious viral particles and transfection of RBL-2H3 cell line and BMMCs were done as recommended by the vendor (Retroviral Gene Transfer and Expression User Manual; BD, Franklin Lakes, N.J.). In brief, the packaging cell line GP2-293 cells were transfected with pVSV-G (BD, Franklin Lakes, N.J.) and pTNF-GFP using lipofectamine 2000 (Invitrogen, Carlsbad, Calif.). Between 48 and 72 h after transfection, viral particles were collected. Healthy RBL-2H3 cells were grown to 50% confluence and then infected by collected viral particles. The infection rate of RBL-2H3 cells was 80-90%. BMMCs were cultured in the presence of 5 ng/mL rIL-3 (R&D Systems, Minneapolis, Minn.) and 5 ng/mL rSCF (R&D Systems, Minneapolis, Minn.). $2 \times 10^5$ cells/mL of healthy and actively dividing BMMCs were infected by the viral particles. The infection rate of BMMCs was around 5-10% because of the fact that these cells grow slowly and in suspension. The TNF-GFP-transfected cells were selected by adding Geneticin (Invitrogen, Carlsbad, Calif.) to a final concentration of 250 μg/mL for 5 d. TNF-GFP-expressing BMMCs were cultured in 5 ng/mL rIL-3 on a monolayer of 3T3 fibroblasts for 10 d before treatment. Both TNF-GFP-expressing cell types were observed after activation with 1 μM ionomycin.

Microscopy.

Whole mount rat mesentery preparations were made by stretching a loop of bowel over a slide so that the transparent windows were spread across them, waiting for these to dry, and then cutting away unwanted tissue. Then they were fixed with cold acetone, permeabilized, and blocked overnight in PBS with 0.3% Triton X-100 and 5% goat serum, and labeled with an anti-LYVE-1 antibody (Millipore, Billerica, Mass.) and fluorophore (Alexa Fluor 488 or TRITC, depending on the experiment)-labeled avidin (Sigma-Aldrich, St. Louis, Mo.) before imaging using a laser-scanning confocal microscope. The LYVE-1 antibody was detected with an FITC-conjugated anti-rabbit IgG F(ab')2 (Jackson ImmunoResearch Laboratories). Some images were made under epifluorescence illumination.

For sections, 10-μm frozen sections were made and fixed in cold acetone before being blocked in PBS with 1% BSA and subsequently labeled with the reagents described in the previous paragraph. For toluidine blue staining, frozen sections were rapidly fixed in 75% methanol, 20% formaldehyde, and 5% acetic acid and then stained in acidic 0.1% toluidine blue and cover slipped.

To create the image showing only metachromatic areas of toluidine blue-stained LN sections, the original image was transformed in Photoshop using the select color range function and visually identifying areas that corresponded to the metachromatic particles. Photoshop was then used to generate an image depicting only those areas, which were verified visually by comparing the original image to the generated image. This program was not used to identify particles but rather to produce an outline of metachromatic areas with more visual contrast for viewing in journal format.

For SEM, rat peritoneal lavage cells were seeded onto polylysine-coated coverslips in RPMI 1640 media with 10% FBS and incubated for 15 min at 37° C. They were then treated with compound 48/80 at 5 μg/mL for 15 min. Finally, the cells were fixed in 3% glutaraldehyde and processed for SEM. Coverslips were postfixed for one hour in 1% OsO4 (in water) before being dehydrated into ethanol and hexamethyldisilazane and finally dried. Then they were mounted and coated with osmium for imaging on a microscope (XL-30 ESEM-FEG; FEI Company).

Immunoblotting.

For the purification of MC granule particles, rat peritoneal cells were treated for 5 min with 5 μg/mL of compound 48/80 in a cell culture incubator. After the treatment, the cells were separated from granule particles by centrifugation at 450 g. The supernatant was carefully removed and thereafter spun at 12,000 g for 10 min at 4° C. to pellet MC-derived particles. These were then solubilized by boiling in Laemmli buffer under reducing conditions, separating the proteins by SDS-PAGE, and transferring to a PDVF membrane. The membrane was blocked for 1 h in 5% milk in TBST and then probed with an anti-TNF antibody (Santa Cruz Biotechnology, Inc., Santa Cruz, Calif.) at 200 ng/mL at 4° C. overnight. The signal was detected using enhanced chemiluminescence.

Microparticles. Synthetic heparin/chitosan particles were generated by gradually combining 1% heparin (EMD) and 1% chitosan (Primex; both in distilled $H_2O$) in a 1:1 ratio at approximately pH 4.5-5. To produce particles, 1 vol of 1% chitosan was added to 5 vol of 1% heparin and vortexed for 30 s. This was repeated until a 1:1 ratio of 1% chitosan to 1% heparin was achieved. After 10 min at room temperature, the pH was then adjusted to neutrality to prevent further aggregation. Particles were centrifuged at 14,000 g for 10 min at 4° C. to form a pellet and washed with water before resuspension in PBS for injections or water for visualization on coverslips. To load particles with TNF, 5 ng rTNF (R&D Systems, Minneapolis, Minn.) was vortexed for 10 min in 1.25 mL 1% heparin before the addition of chitosan as described in this section.

Figure 2:
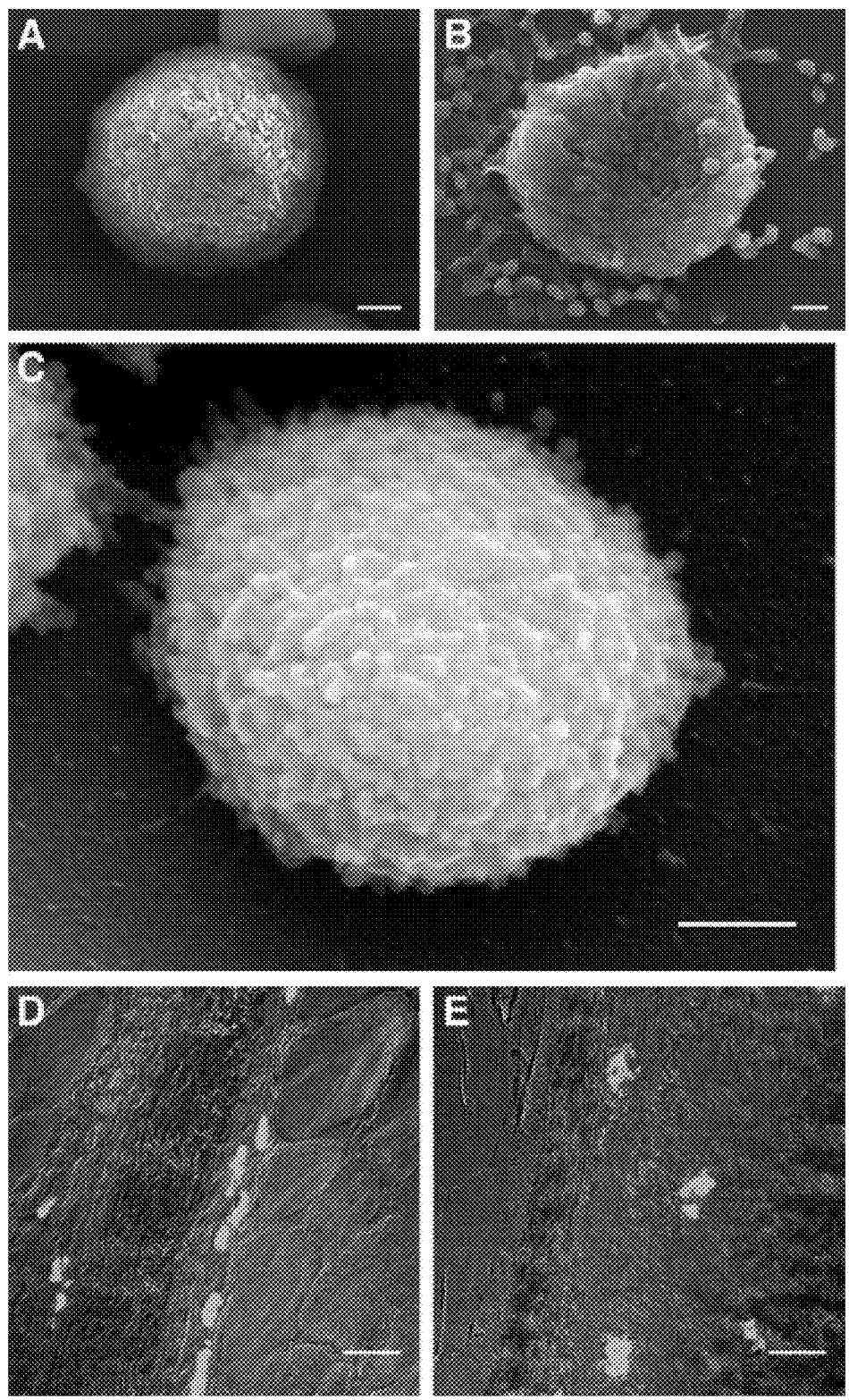
FIG. 2A is an SEM of an unstimulated rat peritoneal MC (rPMC) (bar=2 μm).
FIG. 2B is an SEM of rPMC 15 min after treatment with compound 48/80 at 5 μg/mL (bar=2 μm).
FIG. 2C is an SEM of a single extracellular granule (bar=500 nm).
FIG. 2D is a confocal micrograph of MCs in mouse footpad (granule heparin labeled with Alexa Fluor 488-conjugated avidin) 30 min after PBS injection showing undegranulated MCs (bar=30 μm).
FIG. 2E is an image of mouse footpad MCs surrounded by extracellular particles 30 min after injection of 5 μg of compound 48/80 (bar=30 μm).

Example 2. Activated MCs Release Stable Particles Containing Inflammatory Mediators It was investigated whether MCs released stable particles upon activation. FIG. 2A and FIG. 2B show scanning electron micrographs (SEMs) of isolated rat peritoneal MCs (rPMC) before and after 15 min of exposure to compound 48/80 at 5 µg/mL, a potent small molecule MC activator. After MC activation, a large number of extracellular spherical particles were dispersed around each MC (FIG. 2B), which had a mean diameter of 917 nm (bar=2 µm). Examination at higher magnification (bar=500 µm) revealed that each of these particles was comprised of many smaller, mostly spherical, subunits with a mean diameter of 59.4 nm (FIG. 2C). Release of particles by rat peritoneal MCs was observed repeatedly (in greater than three independent experiments). SEMs are shown from one representative experiment. For some trials (A)-(C), lavage was pooled from multiple rats to obtain sufficient material for analysis. Video microscopy of these events revealed the dynamics of particle release by MCs. Interestingly, particles were released relatively gradually and continued to be shed for at least a minute after treatment.

To demonstrate the release of particles by MCs in vivo, we injected the footpads of mice with 5 µg of compound 48/80 and, 30 min later, thin tissue sections were prepared and examined for MC granule release. The granules were detected with Alexa Fluor 488-conjugated avidin, a probe which selectively binds heparin (Tharp et al., *J. Histochem. Cytochem.* 1985, 33, 27-32), a major constituent of MC granules (FIG. 2D and FIG. 2E, bar=30 µm). Also, when MCs were activated in vivo with another more physiological stimulus, bacterial peptidoglycan, identical particles were released into the surrounding tissue. Significant MC degranulation was observed in the footpad sections and extracellular particles moved significant distances from their parent cells, especially in areas of less dense connective tissue. Observations revealed that 30 min after MC degranulation in vivo, morphologically distinct particles containing heparin could be detectable in the immediate vicinity as well as at considerable distances (up to 150 µm in this section) from the site of release. Some of these extracellular particles were still detectable up to one hour after treatment.

Figure 3:
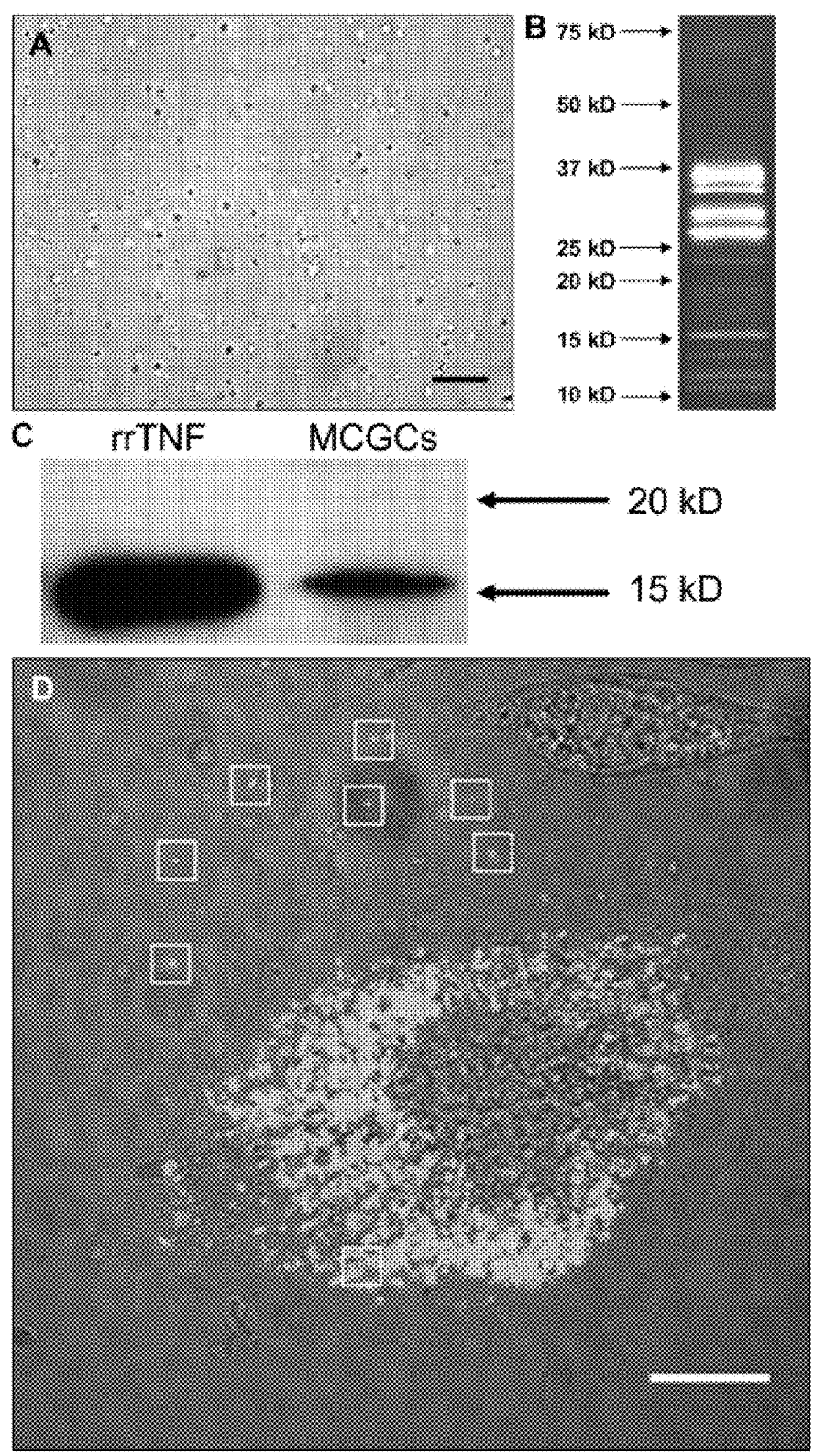
FIG. 3A is a differential interference contrast micrograph of purified MC granule particles.
FIG. 3B is a SYPRO Ruby-stained SDS-PAGE gel of MC particle-associated proteins.
FIG. 3C is a TNF immunoblot of SDS-PAGE-separated proteins from purified particles showing detection of rat TNF.
FIG. 3D is a still image from an extracellular environment showing that particles released from RBL-2H3 cells after activation retain overexpressed TNF-GFP fusion protein (bars, 15 μm), with white boxes highlighting released particles with retained fluorescence.

Next, we attempted to determine whether relevant signaling molecules were present in the particles released by MCs. To investigate this, we purified MC granule particles from rat peritoneal lavage cells using a modification of a previously described technique (Lindstedt et al., *J. Lipid Res.* 1992, 33, 65-75). In brief, the cells were treated with compound 48/80 and the released particles were isolated by differential centrifugation. FIG. 3A shows a differential intereference contrast micrograph of a suspension of purified or isolated MC-derived particles. The purified particles were very stable after isolation, not changing appreciably in appearance or protein composition even after 2 months at room temperature. To determine their bulk protein composition, we subjected them to SDS-PAGE followed by SYPRO Ruby staining (FIG. 3B). The major bands between 25 and 37 kD correspond to the major rat MC proteases, as determined by a proteomic analysis, which are known to be the most abundant protein constituents of MC granules (Lagunoff and Pritzl, *Arch. Biochem. Biophys.* 1976, 173, 554-563). We also used these preparations to address whether signaling molecules, such as TNF, are present in the particles as minor components. Because TNF was shown in earlier studies to be relevant to morphological changes in the DLNs (McLachlan et al., *Nat. Immunol.* 2003, 4, 1199-1205), we were especially interested in the presence of this signaling molecule. An anti-TNF immunoblot of purified granule remnant proteins revealed a band that co-migrated with recombinant rat TNF (FIG. 3C). The identity of this band was confirmed with two additional different anti-TNF antibodies.

Figure 4:
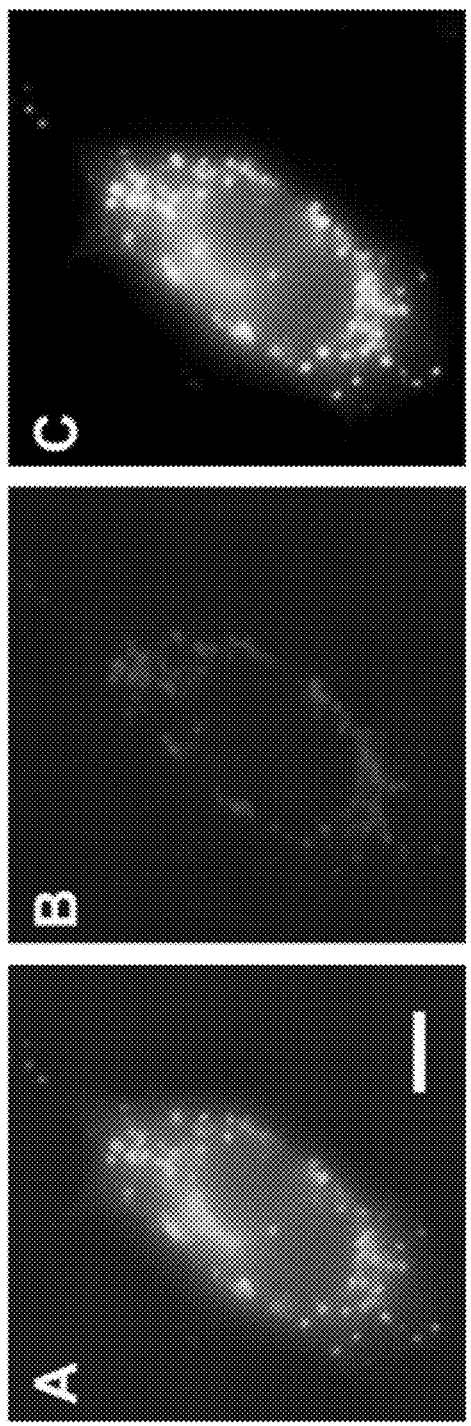
FIG. 4A is an image of vesicles in RBL-2H3 cells showing TNF-GFP expression.
FIG. 4B shows serotonin labeling.
FIG. 4C shows co-localization of the same (bar=5 μm).

To further demonstrate the presence of TNF within released MC-derived particles, we expressed a TNF-GFP fusion protein in the rat MC line RBL-2H3 and in mouse BM-derived MCs (BMMCs) to follow the extracellular fate of preformed TNF after degranulation. In both cases, the fusion protein was clearly localized to vesicles, and it co-localized with known granule markers (FIG. 4). Shown in FIG. 4 are (A) TNF-GFP expression, (B) serotonin labeling, and (C) co-localization (bar=5 µm). After activation, both cell types released free particles that retained their fluorescence (overexpressed TNF-GFO fusion proteins) in the extracellular environment (FIG. 3D). Although the particles released by the cells have not been biochemically characterized, their origin in the granular compartment suggested that they were similar in nature to those released by peritoneal MCs. These findings strongly suggested that TNF released from activated MCs was not freely soluble but remained associated with the granular heparin matrix after exocytosis.

Example 3. MC-Derived Particles Drain to Local LNs Via Lymphatics

In order for MC-derived particles to reach the DLN, they enter lymphatic vessels. Unlike the vascular endothelium, the endothelium of lymphatic capillaries is highly permeable as a result of the presence of discontinuities between individual endothelial cells. These gaps can be larger than a micrometer in diameter and should readily admit objects the size of MC-derived particles (Leak, *Environ. Health Perspect.* 1980, 35, 55-75; Trzewik et al., *FASEB J.* 2001, 15, 1711-1717). Indeed, during edema (which occurs almost instantaneously after MC degranulation because of the rapid action of the completely soluble mediator histamine on vascular permeability), these openings are enlarged as the relative quantity of bulk tissue flow entering the lymphatic system is greatly increased (Casley-Smith, *Lymphology* 1980, 13, 120-129). Thus, it is likely that conditions in the tissue after MC activation favor the entry of these particles into lymphatic vessels.

Figure 5:
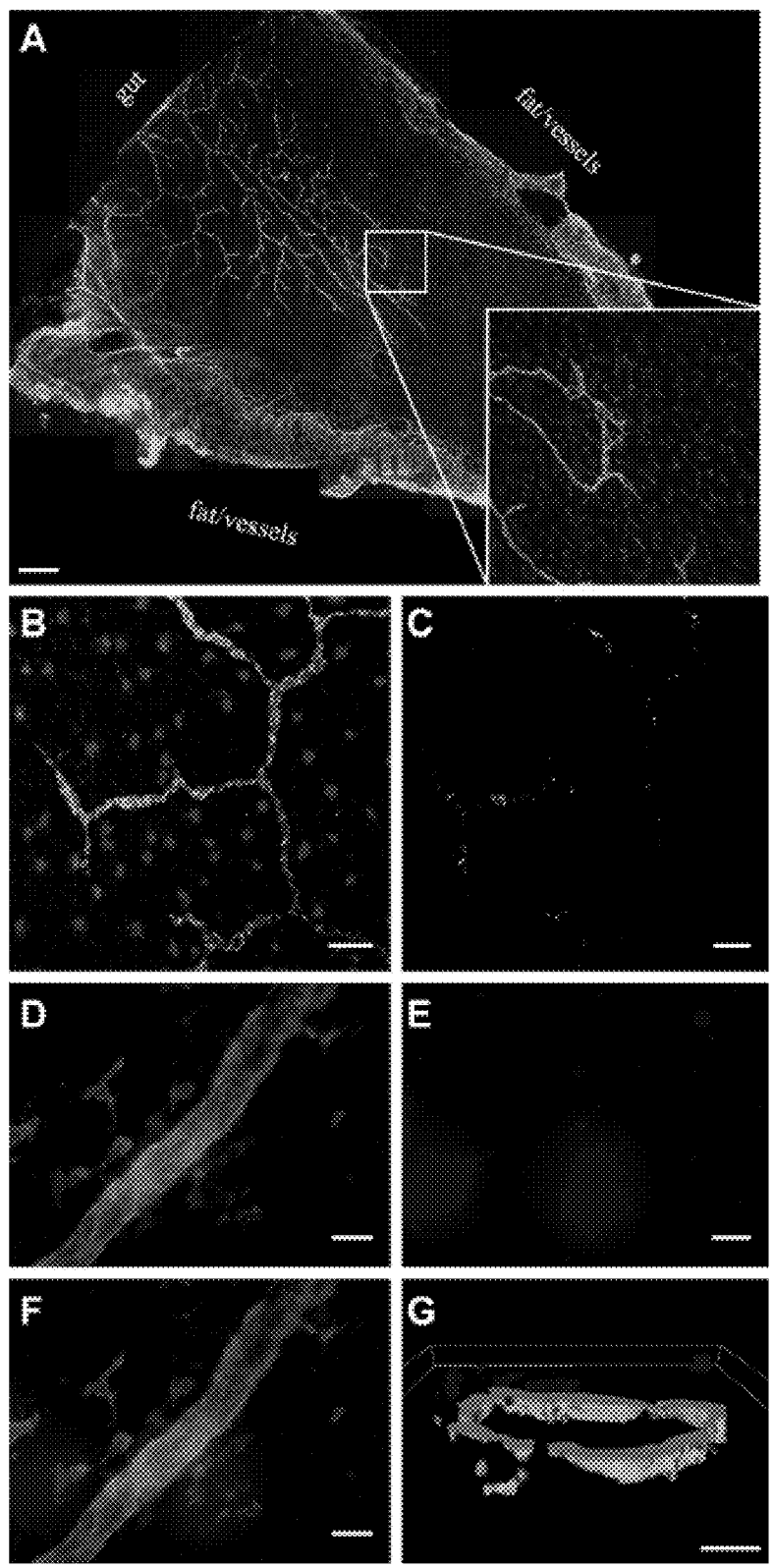
FIG. 5A is a 40× confocal micrograph showing association of MCs and lymphatic capillaries in whole mount rat mesentery preparation.
FIG. 5B is a fluorescence micrograph showing co-localization between released MC-derived particles and lymphatic capillaries 30 min after intraperitoneal injection of 500 μg of compound 48/80.
FIG. 5C is the same area as in B, but only areas of co-localization are shown.
FIG. 5D, FIG. 5E, and FIG. 5F are confocal micrographs of MC granule particles inside a lymphatic capillary in rat mesentery whole mount 30 min after intraperitoneal injection of 500 μg of compound 48/80.
FIG. 5G is an isosurface rendering of confocal volume from mouse footpad section 30 min after injection of compound 48/80.
Figure 6:
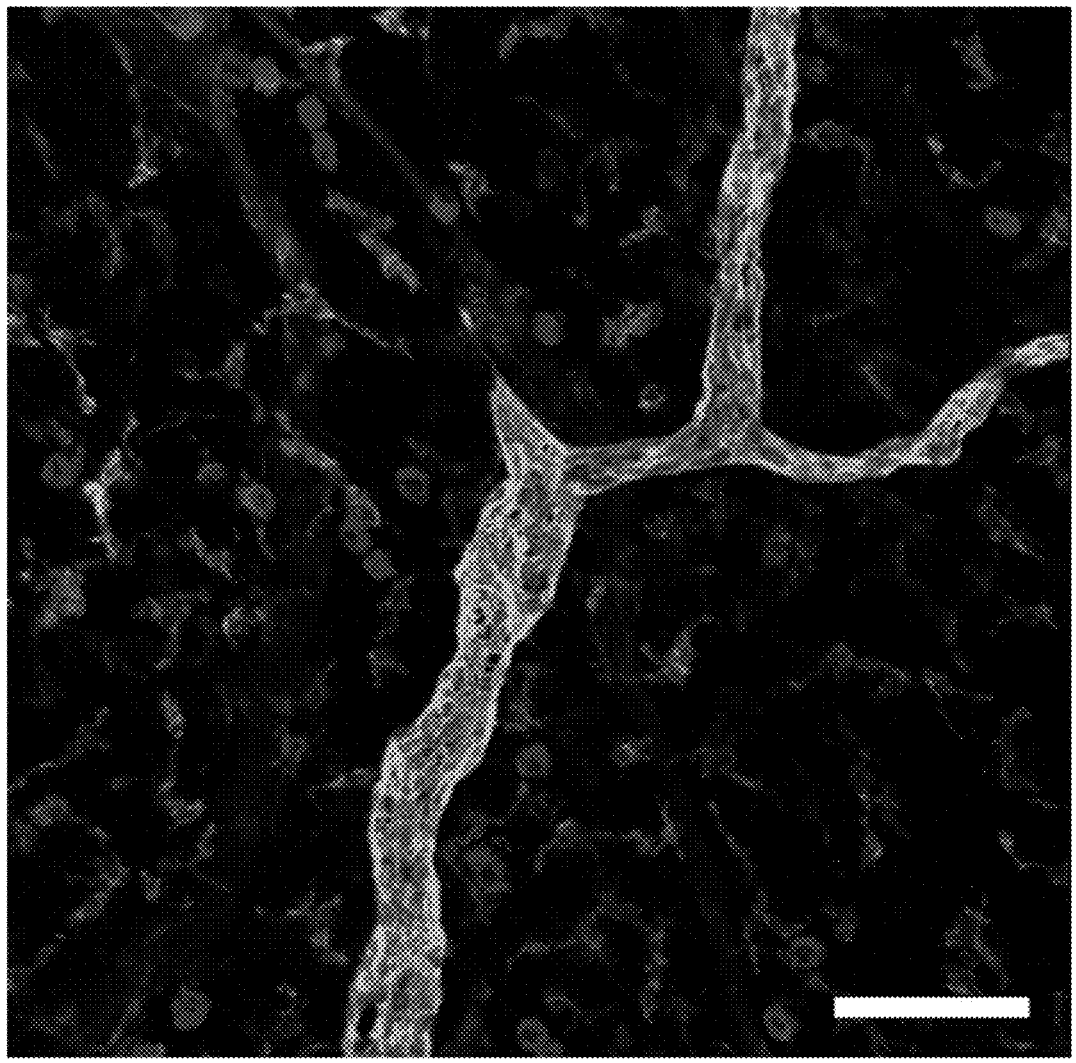
FIG. 6 is an image showing intact MCs in untreated rat mesentery.
Figure 7:
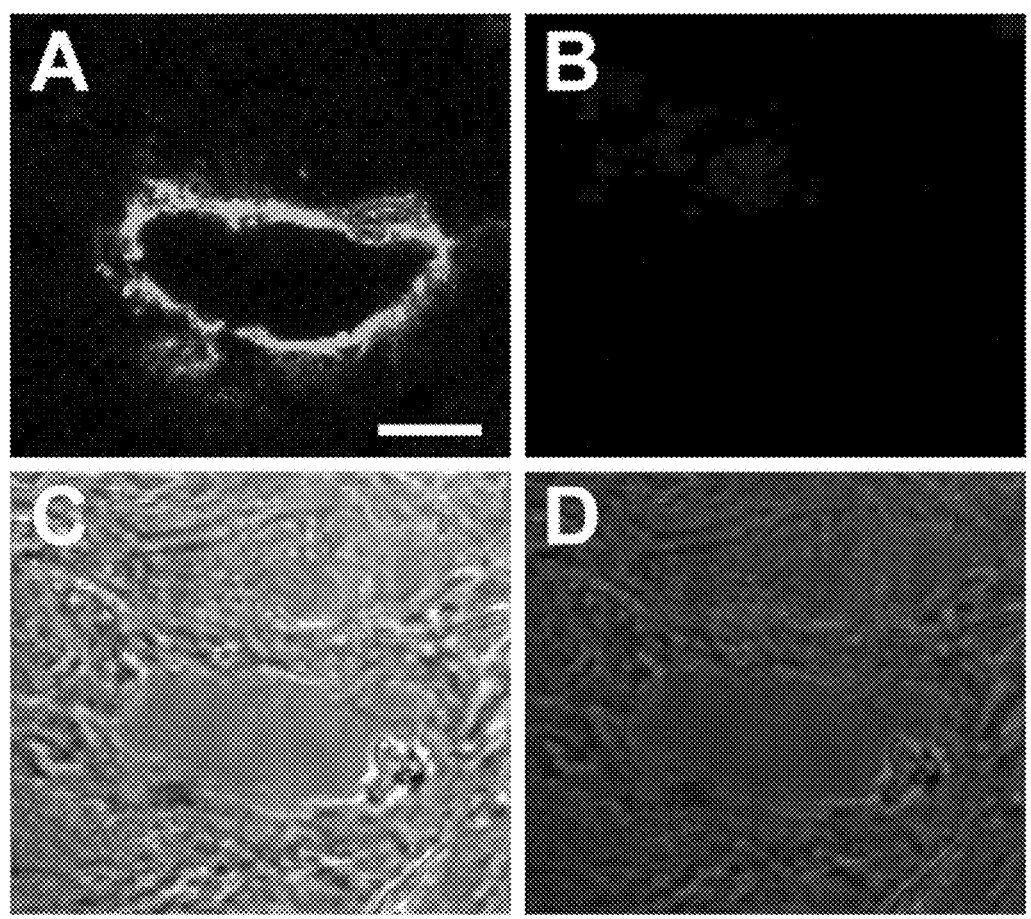
FIG. 7A-D are images of luminal side of the endothelium of mouse footpad showing that MC-derived particle is not inside a migratory phagocyte.

To visualize this process, we focused on the rat mesentery, because it was amenable to observation in whole mount, allowing the entire lymphatic network and connective tissue drainage to be visualized (FIG. 5A). Shown in FIG. 5A is a mosaic of 40× confocal micrographs showing association of MCs and lymphatic capillaries in whole mount rat mesentery preparation (inset is 5× magnified view; green, LYVE-1; blue, MC heparin; bar=1 mm). In mesentery isolated 30 min after the intraperitoneal instillation of compound 48/80, extensive MC degranulation occurred, and clear co-localization between extracellular MC granule particles and lymphatic capillaries was observed along the length of lymphatic vessels (FIG. 5B and FIG. 5C). Shown in FIG. 5B is fluorescence micrograph showing co-localization between released MC-derived particles and lymphatic capillaries 30 min after intraperitoneal injection of 500 μg of compound 48/80 (green, LYVE-1; red, MC heparin; bar=25 μm). FIG. 5C is the same as in FIG. 5B, but only areas of co-localization are shown. In contrast, there was little to no degranulation in untreated rat mesentery (FIG. 6; green, LYVE-1; red, heparin; bar=125 μm). Close examination of lymphatic vessels in compound 48/80-treated rats (30 min after intraperitoneal injection of 500 μg of compound 48/80), such as the area proximal to the two degranulated MCs shown in FIG. 5D and FIG. 5F, revealed that MC particles appeared frequently in the center of the vessel surrounded entirely by staining for lymphatic markers. However, because the lymphatic vessels in these preparations were collapsed, it was not possible to definitively demonstrate the presence of the particles within them, although it was unlikely that there is much space outside the vessels given the extreme thinness of the tissue (15-20 μm; Barber et al., *Am. J. Physiol.* 1987, 253, G549-G556). So, to corroborate these data with cross-sectioned patient lymphatic vessels, we returned to the mouse footpad. Dilated lymphatics were frequently seen in this tissue 30 min after the injection of compound 48/80. We clearly observed MC-derived particles on the luminal side of the endothelium (FIG. 5G, showing isosurface rendering of confocal volume from mouse footpad section 30 min after injection of compound 48/80; 3D reconstructions of this area imaged with laser scanning confocal microscopy; green, LYVE-1; blue, MC heparin; bar=8 μm). DIC microscopy of the same area revealed that the particle shown in FIG. 5G was not inside a migrating phagocyte but was apparently moving as a free particle (FIG. 7). Shown in FIG. 7 are (A) green, LYVE-1; (B) blue, heparin; (C) differential contrast interference micrograph of local morphology; and (D) DIC image and heparin signal superimposed (bar=8 μm). Together, these images suggested that MC-derived particles can gain access to and traffic within the lymphatic system.

Figure 8:
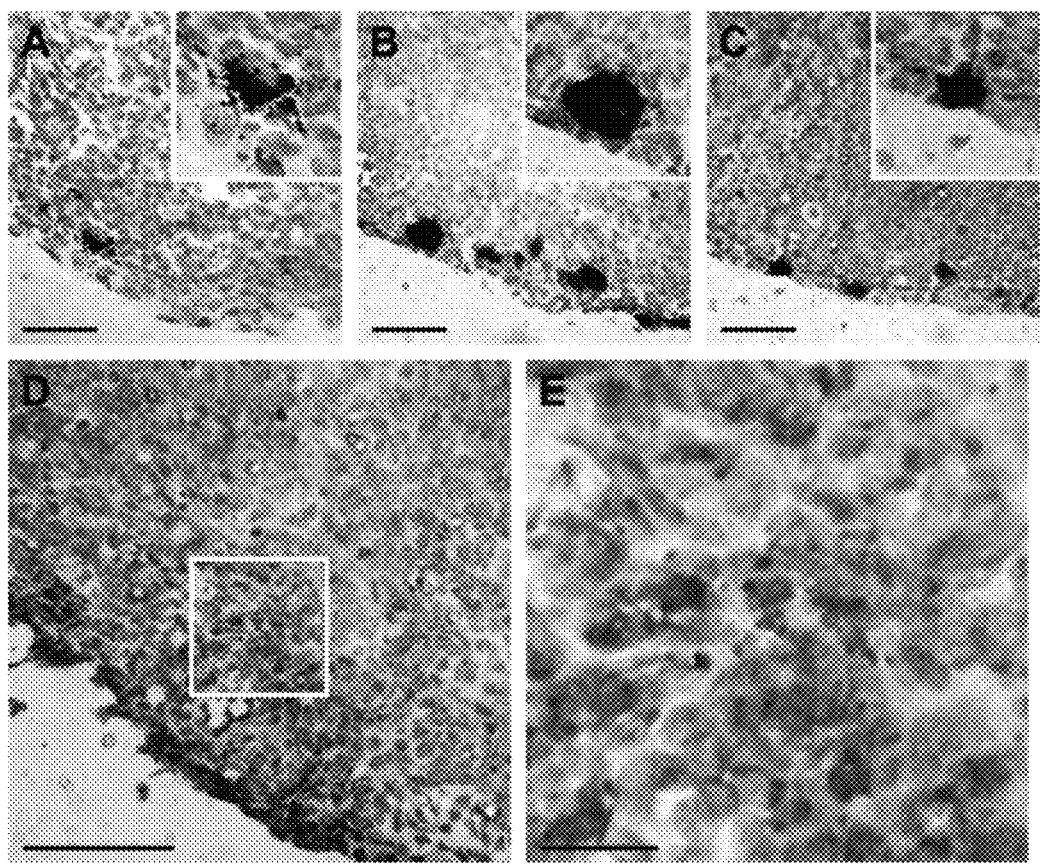
FIG. 8A, FIG. 8B, and FIG. 8C are toluidine blue-stained sections of DLN tissue 2 h after injection with 32 μg of compound 48/80, topical application of vehicle alone, or topical application of 10 μg PMA.
FIG. 8D is an image of free metachromatic granules within the DLNs of PMA-treated footpads.
FIG. 8E is the magnified view of the white box in FIG. 8D.

Next, we sought to demonstrate that the MC particles could reach DLNs from the periphery. Our initial attempts to detect MC particles trafficking from footpads to DLNs was confounded by the fact that the MC activator compound 48/80 that we had injected not only activated tissue resident MCs but had also drained into the DLNs, causing degranulation of LN-resident MCs (FIG. 8A). Therefore, we selectively activated peripheral MCs in the skin by painting the footpads with a solution PMA in acetone (Wershil et al., *J. Immunol.* 1988, 140, 2356-2360). This treatment caused local degranulation. Footpad MCs were intact after painting with acetone alone. Next, we examined the DLNs to see if the observed MC degranulation was selective to the site of application. In contrast to DLNs harvested 2 h after administration of compound 48/80, where extensive degranulation of LN MCs occurred (FIG. 8A), the LN-resident MCs of mice after PMA treatment (FIG. 8C) appeared similar to vehicle alone (FIG. 8B), without apparent degranulation.

Shown in FIG. 8A are toluidine blue-stained sections of DLN tissue 2 h after injection with 32 μg of compound 48/80 with topical application of vehicle alone. FIG. 8B is the same as FIG. 8A but showing only metachromatic staining, with the location of the edge of the DLN depicted by a dashed line. Shown in FIG. 8C is a magnification from the square in FIG. 8A, bar=10 μm. Having confirmed that the topical application of PMA selectively activated footpad MCs, we examined the DLNs more closely and observed numerous metachromatic (heparin containing) particles in the periphery of the same LN section shown in FIG. 8C and FIG. 8D). FIG. 8DE shows free metachromatic granules could be visualized within the DLNs of PMA-treated footpads, wherein FIG. 8E (bar=20 μm) is the magnified view of the white box in FIG. 8D (bar=50 μm). The subcapsular and cortical sinuses, also at the edge of the LN, are the first to receive peripheral lymph from afferent lymphatics. A higher magnification of a selected area of the DLN shows several individual particles (FIG. 8E).

Figure 9:
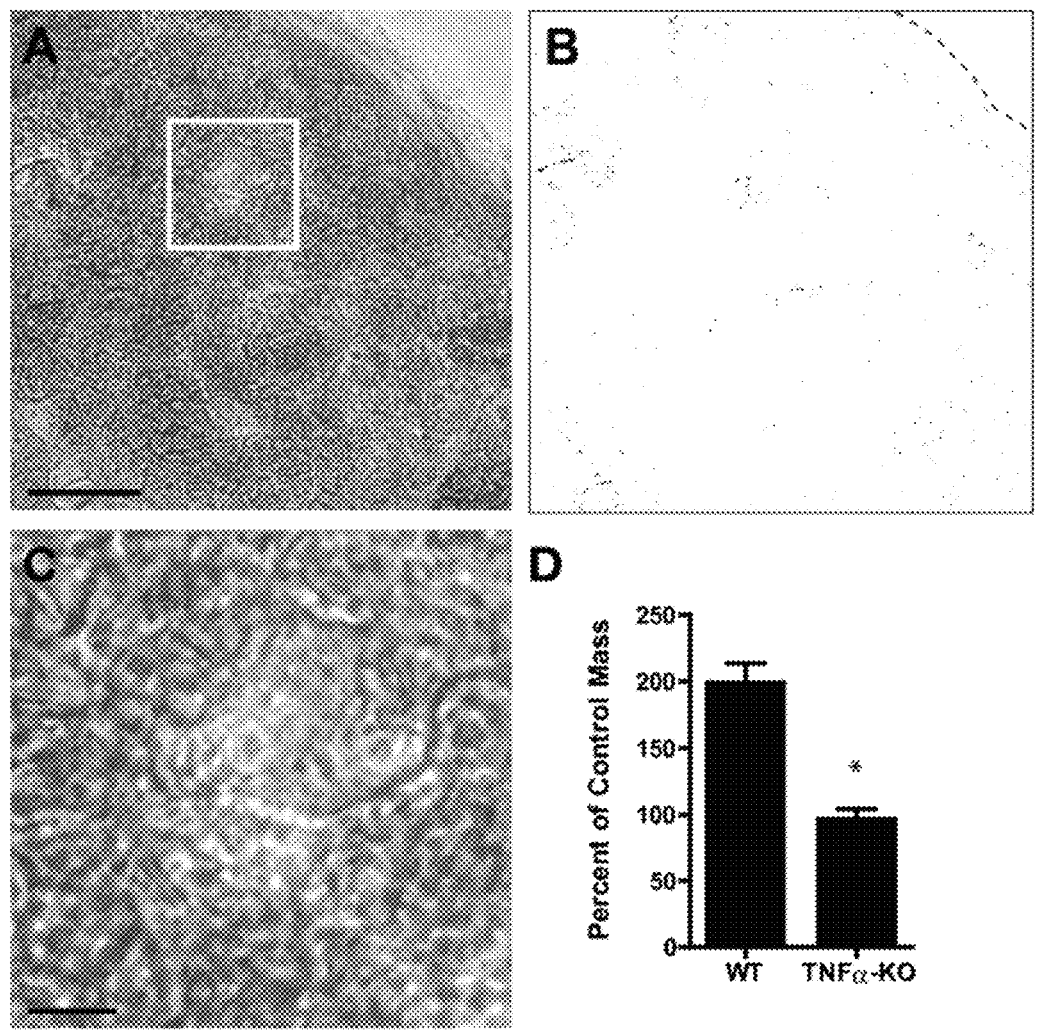
FIG. 9A is a toluidine blue staining image of DLN tissue sections from an MC-deficient KitW-sh/W-sh mouse injected with $9.0\times10^3$ isolated MC-derived particles.
FIG. 9B is the same area as in FIG. 9A showing only metachromatic staining.
FIG. 9C is a magnification from square in FIG. 9A.
FIG. 9D is a graph showing LN hypertrophy 24 h after injection of $1.5\times10^4$ particles purified from WT or $TNF^{-/-}$ mice.

To support our conclusion that particles detected in the DLNs originated from the periphery and to determine that these particles could traffic from peripheral sites to the DLN, we isolated particles from the peritoneal MCs of mice. These particles were injected into the footpads of MC deficient KitW-sh/W-sh mice. DLNs were isolated 45 min later and cross sections were examined for the presence of granules after toluidine blue staining. At this early time point, it was extremely unlikely that the observed particles were delivered to the LN inside migrating cells, as the processes involved in migrating through tissues and across the lymphatic endothelium are complex and require changes in gene expression. Distinct particles appeared to be widely distributed in the cortical and medullary sinuses of the DLNs (FIG. 9A and FIG. 9B). FIG. 9A shows toluidine blue staining of DLN tissue sections from an MC-deficient KitW-sh/W-sh mouse injected with $9.0 \times 10^3$ isolated MC-derived particles (bar=50 μm), and FIG. 9B shows the area as in FIG. 9A but showing only metachromatic staining. The location of the edge of the DLN is depicted by a dashed line. A close-up (bar=10 μm) showing a cluster of metachromatic particles in the periphery of the DLN is shown in FIG. 9C. To exclude the possibility that particles of this size only enter lymphatic vessels under conditions of nonphysiologic interstitial pressure (as a result of injection), we painted a footpad laceration with a suspension of fluorescent microspheres with the same size and surface charge characteristics of MC-derived particles.

Figure 10:
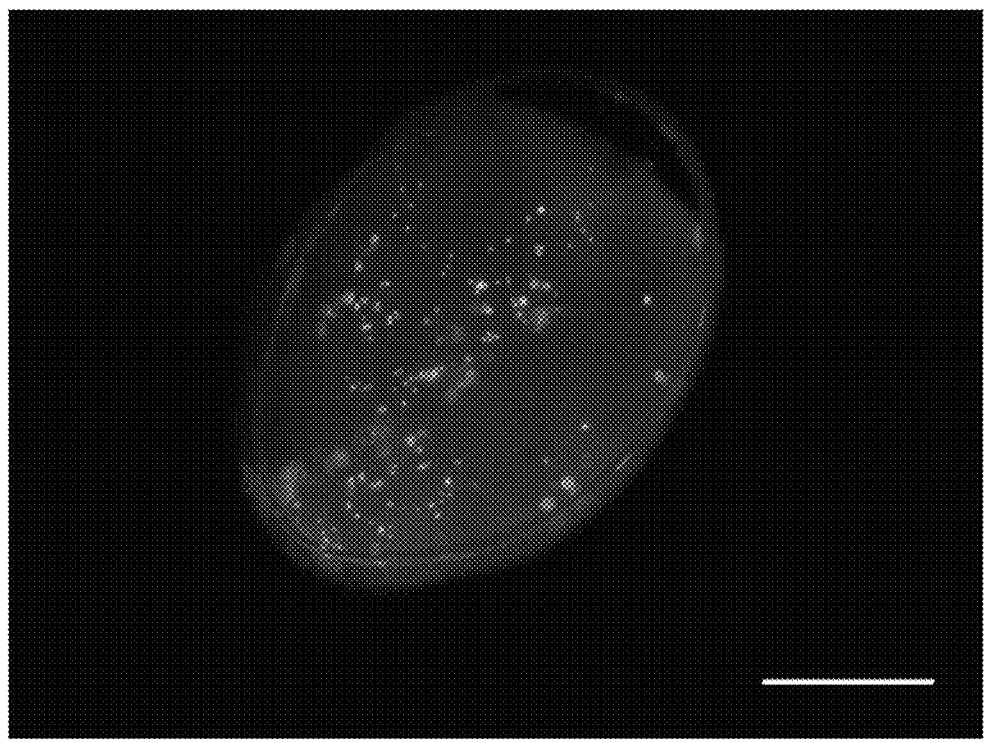
FIG. 10 is an epifluorescence micrograph of whole-mounted mouse popliteal LN 30 min after the introduction of fluorescent microspheres into an experimental laceration.
Figure 11:
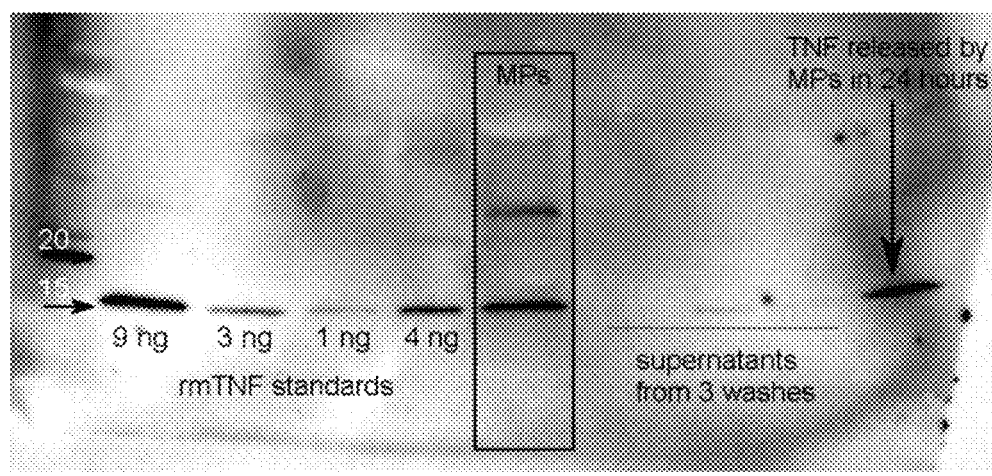
FIG. 11 is an immunoblot showing the disposition of recombinant mouse TNF (rmTNF) during encapsulation.

Microspheres were found in the DLN only 30 min later, indicating that they entered lymphatic vessels and were delivered by lymph (FIG. 10). FIG. 10 shows an epifluorescence micrograph of whole-mounted mouse popliteal LN 30 min after the introduction of fluorescent microspheres into an experimental laceration (bar=250 μm). FIG. 11 shows that recombinant TNF was gradually released from heparin-based microparticles. In FIG. 11 is an immunoblot showing the disposition of recombinant mouse TNF (rmTNF) during encapsulation. After the initial precipitation of the particles, they were washed three times with the same volume PBS. The particles were then allowed to stand for 24 h at room temperature, after which they were sedimented a final time. The sediment (MP-associated TNF) is shown in the boxed lane. The supernatant (TNF released from MPs over 24 h) is shown in the right lane. The five left lanes show a molecular size standard and quantitation standards of known amounts of rmTNF. Collectively, these experiments indicated that MC particles readily trafficked to the DLNs via the lymphatic system.

Example 4. Particle-Associated TNF Elicits LN Enlargement

We examined the effect of footpad injection of MC particles on LN remodeling to evaluate whether peripheral MCs are able to modulate important physiological activities at distal sites through the release of particles bearing critical mediators. To demonstrate the specific contribution of TNF, we injected an equal number of particles isolated from $TNF^{-/-}$ mice in a parallel experiment. The LN hypertrophy induced by granules from WT and $TNF^{-/-}$ animals was compared after 24 h to saline-injected controls. Although MC particles from wild-type mice induced a twofold increase in LN size, particles from $TNF^{-/-}$ mice failed to trigger any LN hypertrophy (FIG. 9D). FIG. 9D shows LN hypertrophy 24 h after injection of $1.5 \times 10^4$ particles purified from WT or $TNF^{-/-}$ mice (n=3 for each group; *, P<0.005 for the comparison between the two groups; data analyzed by unpaired two-tailed Student's t test; error bars indicate standard error of the mean). This finding not only demonstrated a functional role for MC-derived particles but also demonstrated the specific role played by TNF bound within them in modulating LN hypertrophy.

Figure 12:
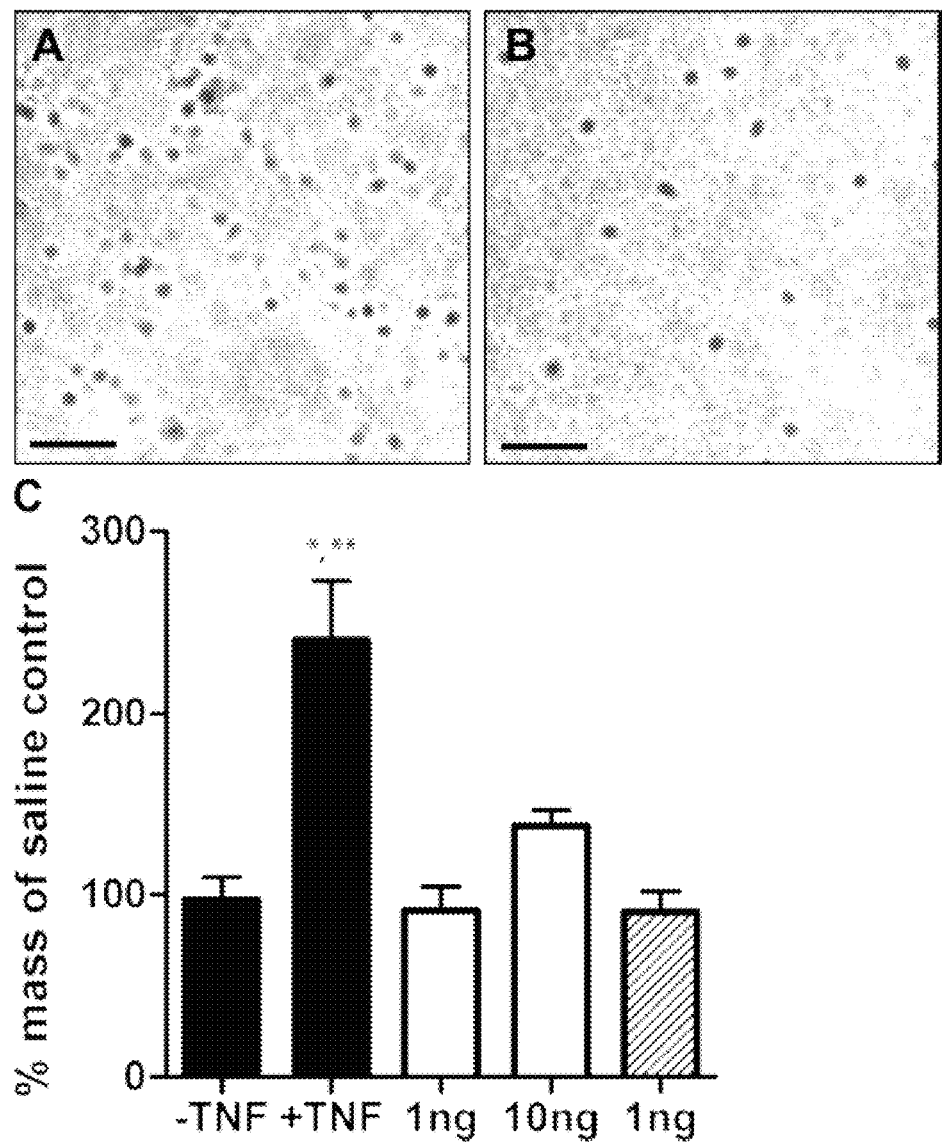
FIG. 12A is a DIC micrograph showing purified rat MC-derived particles.
FIG. 12B is a micrograph showing synthetic heparin/chitosan microparticles.
FIG. 12C is a graph showing LN enlargement for samples injected into the footpads of mice (black bars, particles with and without encapsulated TNF; open bars, soluble TNF; hatched bar, soluble TNF mixed with soluble chitosan and heparin.
Figure 13:
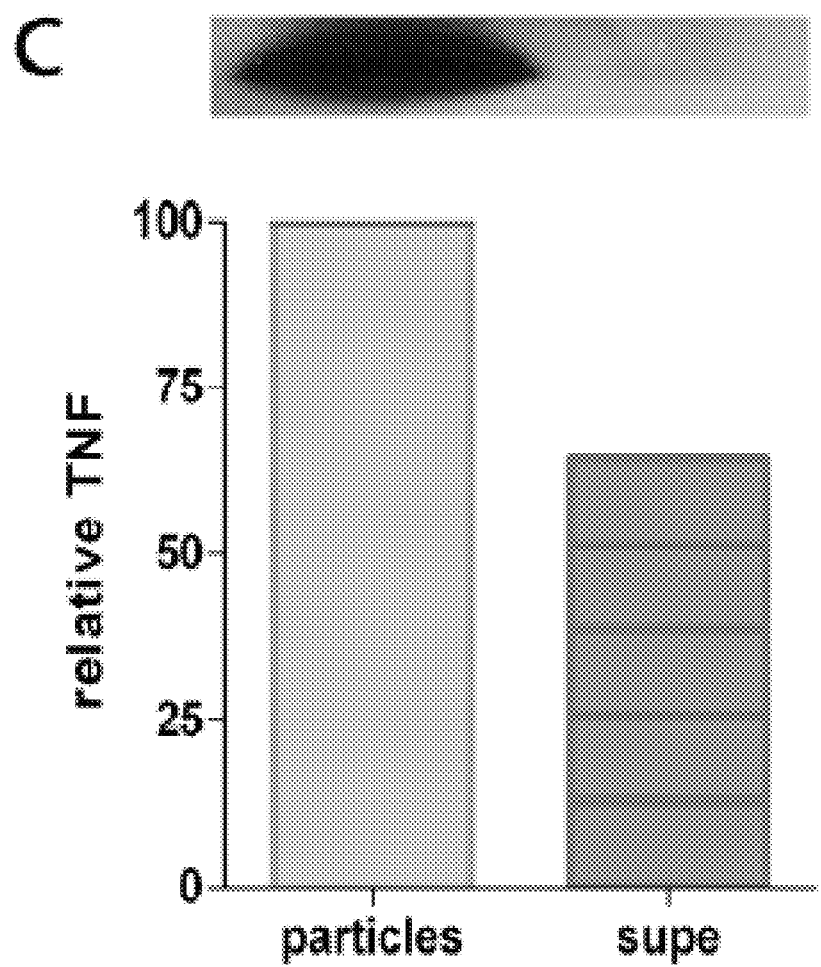
FIG. 13 is a Western blot (top) of synthetic particles (left band) for encapsulated TNF and the supernatant after 24 hours at room temperature (right band), demonstrating mediator release, with a graph of the percent release determined by densitometry.

We compared soluble recombinant TNF to TNF encapsulated within synthetic heparin/chitosan particles for their ability to effect remodeling of DLNs to evaluate whether by being packaged within stable particles, MC mediators, are protected from dilution and degradation. This also provided that minimal amounts of cytokine (e.g., TNF) can promote biological activity at their target sites. As mentioned previously, heparin has a very high negative charge density. Chitosan, in contrast, is a polycation at pH <5.5 because of protonation of the amino groups in the side chains of the polysaccharide. When solutions containing these compounds are mixed, they rapidly phase separate to form spherical particles because of electrostatic interaction of the oppositely charged heparin and chitosan. This same process, called polyelectrolyte complexation, is thought to be the mechanism by which insoluble complexes are formed in MC granules, only with highly basic MC proteases substituting for chitosan as the polycation (Schwartz et al., *J. Immunol.* 1981, 126, 2071-2078). Since chitosan becomes protonated at acidic pH, giving it a positive charge, modulation of the pH can influence the extent of complexation, control the size of aggregates, and ensure the stability of particles when the solution is returned to normal pH. Optimizing this parameter resulted in stable particles of relatively uniform size that closely approximated the size of purified MC-derived particles. The resulting particles were similar in size to those purified from rat MCs (FIG. 12A and FIG. 12B). Shown in FIG. 12A is a DIC micrograph of purified rat MC-derived particles, and FIG. 12B is a micrograph showing synthetic heparin/chitosan microparticles (bar=10 µm). Because any molecules bound to heparin or chitosan before the mixing can be packaged within, we encapsulated recombinant TNF (rTNF) in synthetic particles by adding the mediator to the heparin solution before complexation. Using western blot analysis, it was demonstrated that the particles were capable of encapsulating TNA, which can be released into soluble form (FIG. 13). FIG. 13 shows Western blot (top) of synthetic particles (left band) for encapsulated TNF and the supernatant after 24 hours at room temperature (right band), demonstrating mediator release, and percent release determined by densitometry is depicted in the graph below.

Figure 14:
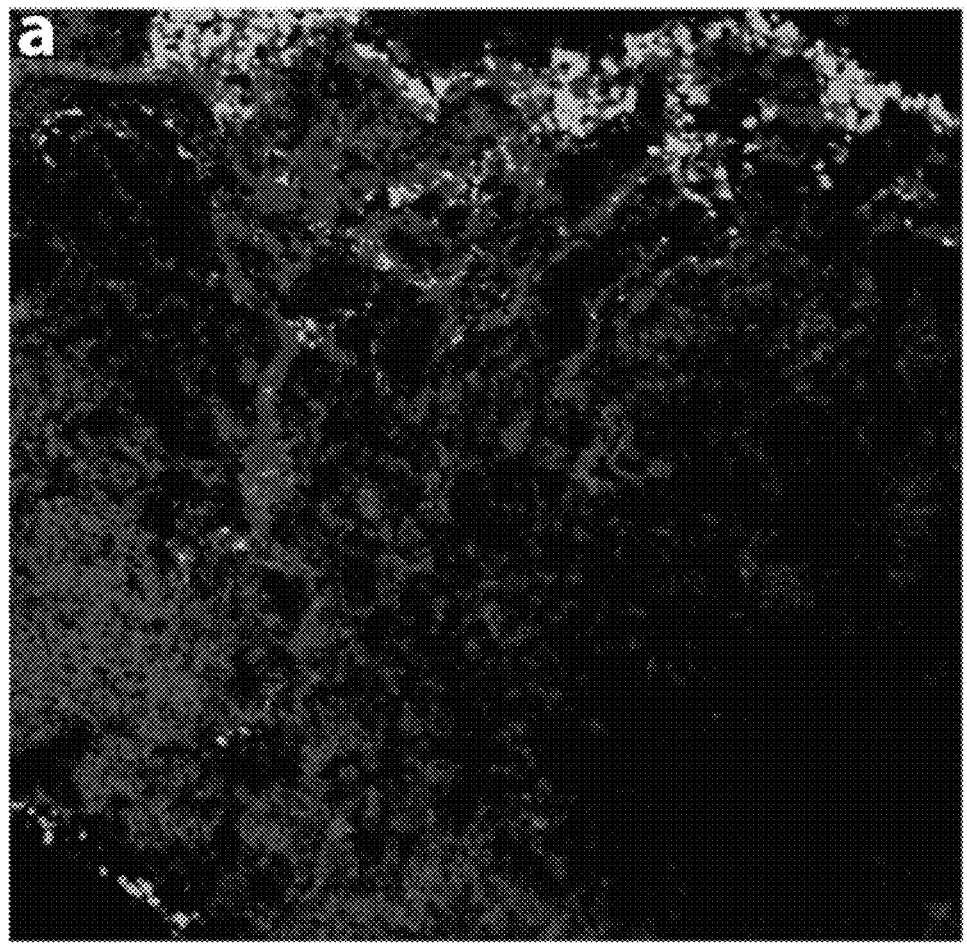
FIG. 14 is a confocal image demonstrating the localization of footpad-injected FITC-labeled heparin-chitosan particles in DLNs in the subcapsular and medullary sinuses (blue, LYVE-1), surrounded by B cells (B220, red), 45 min after injection.

To determine if our synthetic particles could replicate the functions and in vivo targeting characteristics of natural MC particles, we injected these particles into the rear footpads of mice, prior to isolating and examining the footpad DLN, the popliteal node. Footpad-injected particles quickly traveled to the DLN, where they could be visualized in the subcapsular and medullary sinuses (FIG. 14), a distribution pattern similar to that of released peripherally-derived MC particles. FIG. 14 is a confocal image demonstrating the localization of footpad injected FITC-labeled heparin-chitosan particles in DLNs in the subcapsular and medullary sinuses (blue, LYVE-1), surrounded by B cells (B220, red), 45 min after injection.

It was also demonstrated that cytokines encapsulated in heparin-chitosan particles can have functional effects in the DLN, inducing swelling of the DLN, similarly to MC-derived particles. Notably, these results also demonstrated that the particulate delivery of TNF greatly enhanced the activity of this cytokine, allowing it to have at least 10 times greater potency than an equivalent amount of soluble cytokine. As shown in FIG. 12C, the delivery of TNF in particle form increased its potency for causing LN enlargement by >10-fold. FIG. 12C shows than 1 ng rTNF encapsulated in ~$1.3 \times 10^5$ synthetic particles similar to MC granule particles elicited more LN enlargement than 10 ng of soluble TNF when injected into the footpads of mice (black bars, particles with and without encapsulated TNF; open bars, soluble TNF; hatched bar, soluble TNF mixed with soluble chitosan and heparin; n=3 for each group; *, P<0.05 vs. 10 ng soluble TNF; **, P<0.01 vs. particles without TNF, 1 ng soluble TNF, and 1 ng soluble TNF mixed with soluble chitosan and heparin; data analyzed by one-way analysis of variance followed by Tukey's Multiple Comparisons test; error bars indicate standard error of the mean). As the amount of TNF encapsulated was not directly measured, the 1-ng dose shown assumes 100% encapsulation. Other experiments performed during the development of these particles suggested that the true level of encapsulation using this protocol was almost never >30%, indicating that the 10-fold difference in potency between particle-delivered TNF and soluble TNF was a significant underestimate. In a separate experiment, we observed that even as little as 16 µg of TNF could elicit LN hypertrophy when delivered in particle form, supporting previous findings that the early increases in DLN TNF reflect the movement of a very small amount of cytokine (McLachlan et al., *Nat. Immunol.* 2003, 4, 1199-1205).

In addition, microparticles fabricated in exactly the same way except for the omission of TNF did not cause LN enlargement (FIG. 12C), showing that TNF, and not the delivery vehicle, was responsible for the observed effects. Likewise, the injection of a mixture of the soluble components (combined under pH conditions under which no particles form) was not adequate to elicit LN enlargement (FIG. 12C). Collectively, these findings reveal that, when packaged within particles of similar composition as MC particles, minimal amounts of TNF applied in the periphery can induce significant remodeling of distal DLNs.

Figure 15:
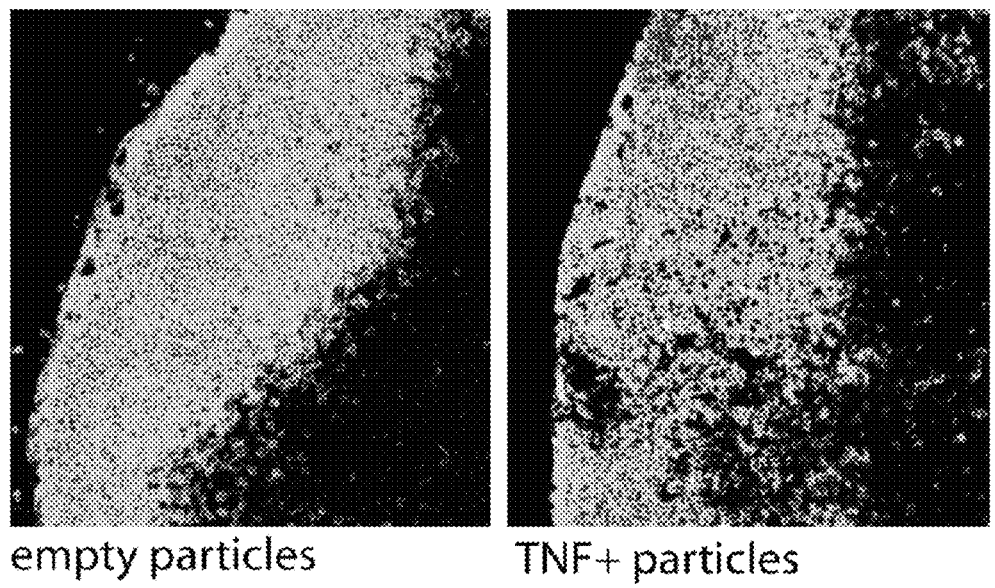
FIG. 15 are images of B cell zones in DLN sections at day 7, stained for B cells (B220, green), IgD (blue), and GL7 (GC marker, red), after administration of soluble protective antigen from B. anthracis in combination with empty or TNF-loaded particles.

Preliminary data also suggested that particulate delivery of TNF with antigen could promote germinal center (GC) production, a key step in the development of high affinity antibodies (FIG. 15). FIG. 15 shows GCs form in DLNs when TNF loaded particles were used as adjuvants, in that mice were administered soluble protective antigen from *B. anthracis* in combination with empty or TNF-loaded particles. Images show B cell zones in DLN sections at day 7, stained for B cells (B220, green), IgD (blue), and GL7 (GC marker, red). Note the halo of IgD downregulation, signifying GC formation and presence of GL7+ cells with particulate TNF administration. These findings raised the potential of applying cytokines, which are costly to produce, as a realistic adjuvant, since only minute quantities would be needed to observe their effects.

Example 5. Particulate Delivery of IL-12

Figure 16:
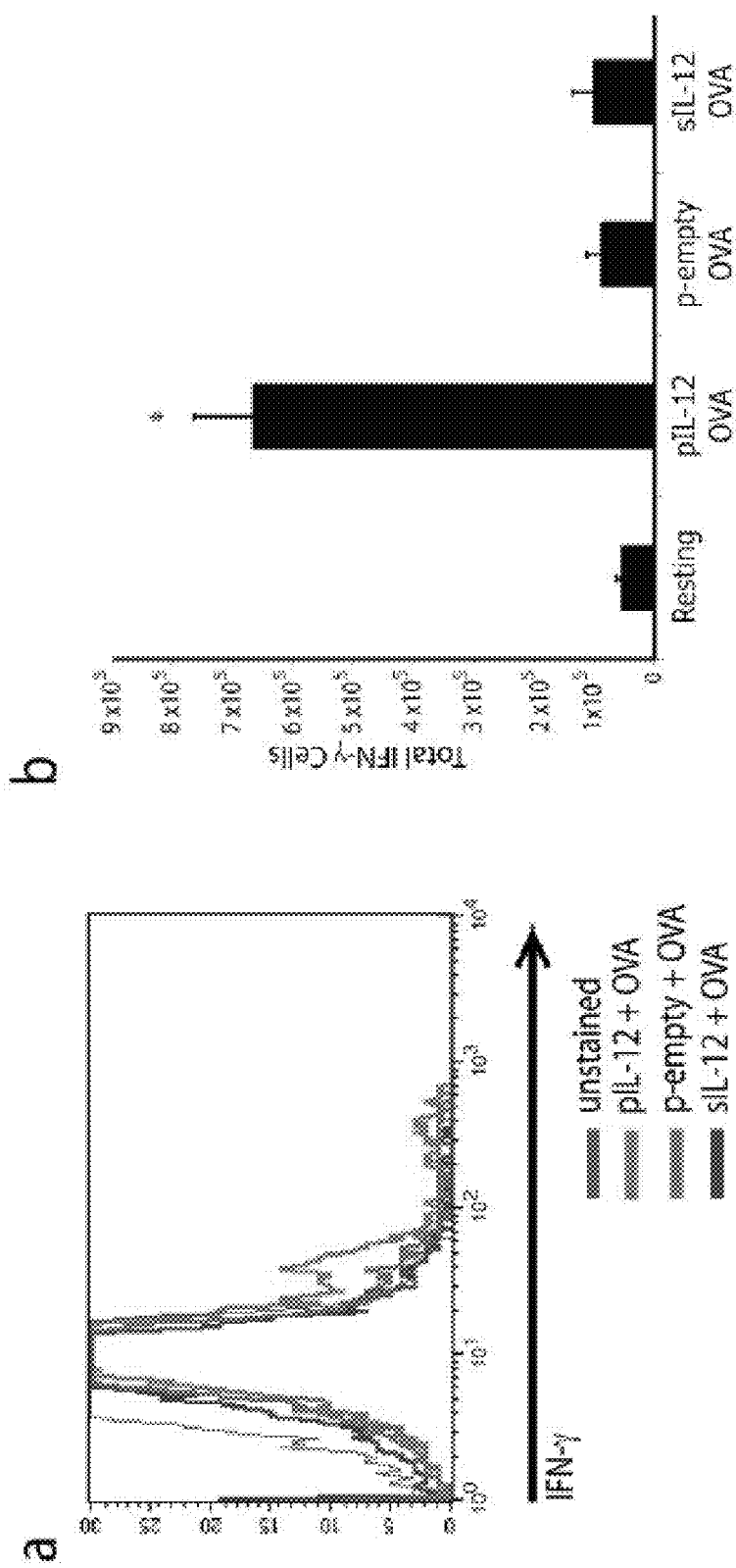
FIG. 16A is a graph showing the number of IFN-γ producing T cells in DLNs quantified by flow cytometry 24 hours after footpad injection of soluble OVA alone, soluble OVA with empty particles, soluble OVA with soluble IL-12, or soluble OVA with particulate IL-12.
FIG. 16B is a graph of the total numbers of IFN-γ producing cells for each sample.

Although TNF has been the target of previous studies due to its incorporation in natural MC-derived particles, other cytokines have been shown to have adjuvant activity and could be potentially targeted to DLNs by applying the MC's strategy. To determine if the activity of another cytokine can be enhanced by its incorporation in DLN-targeting heparin-chitosan complexes, IL-12, a DC-produced cytokine that can drive cell-mediated immune responses, and is associated with viral infection clearance was used to evaluate whether another cytokine can be enhanced by its incorporation in DLN-targeting heparin-chitosan complexes. Injection of particulate IL-12 in conjunction with the soluble experimental antigen, ovalbumin (OVA), greatly increased the number of DLN T cells producing IFN-y by 24 hours, while soluble IL-12 or particles alone did not (FIG. 16). FIG. 16A shows the delivery of particulate IL-12 (pIL-12) enhanced IFN-$\gamma$ production in draining LN T cells, 24 hours after vaccination (footpad injection) with OVA, in contrast to controls of soluble IL-12 (sIL-12) with OVA, or empty particles (p-empty) with OVA. FIG. 16B shows the quantification of IFN-$\gamma$ producing CD3+ T cells that were administered soluble OVA with either soluble or particulate delivery of TNF ($P<0.05$ and error bars signify the standard error where n=3). This effect was further augmented in combination with particulate TNF (data not shown). These results demonstrate that differential loading of our synthetic particles that are modeled after MC granules may be an effective way to target minute quantities of cytokines to the draining LN during vaccination, and the loaded cytokines need not conform to the template provided by MC granules. As a result, the cytokines delivered in particulate form and the resulting polarization of immune responses in the draining LN could be tailored to meet the requirements for protection against an individual challenge.

Example 6. Bioengineered Nanoparticles as Adjuvants

To assess the adjuvant activity of the cytokine-loaded chitosan-heparin nanoparticles described in the previous Examples, we will inject mice intramuscularly with these particles, in conjunction with the current inactivated flu vaccine that contains killed influenza A and B viruses. Appropriate controls will be administered to additional mice, including empty particles, soluble cytokines alone, the existing flu vaccine alone, and the existing flu vaccine along with the positive control of alum. Select combinations of cytokines will be tested for their ability to act as adjuvants when encapsulated in particulate form, including TNF alone, TNF in combination with IL-12, and IL-12 in combination with IL-1$\alpha$ and IL-18. Immunized mice will be boosted with a second injection at 21 days, and blood will be collected at 7, 14, 21, and 42 days after challenge to determine the flu-specific antibody endpoint titers in the sera of immunized mice by ELISA. At these time points, tissues from additional mice will be harvested for histo-pathological analysis by hemotoxylin and eosin staining. It will be expected that the cytokine loaded particles will function similarly to natural MC-derived particles and promote optimal adaptive immune responses to flu vaccine that far exceed the responses observed in mice without adjuvant included. Additionally, we will compare the relative titers of immunoglobulin subclasses, including IgG1 and IgG2a to determine if certain heparin-chitosan complexed cytokines can influence the humoral response. Any observed differences or skewing of the antibody responses resulting from the controlled delivery of various mediators is expected to allow for tailoring the adjuvant activity to the optimal response for an individual infection, whether for the flu or other infective agent, or another vaccine application.

T cell responses will be observed after vaccination against influenza using the groups outlined above. Spleen cells will be isolated and tested for their ability to proliferate or produce cytokines in response to inactivated flu virus exposure in culture. Isolated splenocytes will be cultured in media in the presence or absence of killed viral particles for 5 days, after which the supernatant will be assayed for cytokine production, including IL-2, IL-4, IL-5, IL-17, and IFN-$\gamma$ by multiplex bead assays (Biorad Bioplex). Additionally, splenocytes will be assayed for antigen specific T cell proliferation using Cell Titer 96 (Promega, Madison Wis.), according to the manufacturer's instructions. This assay allows cell viability and antigen-specific T cell proliferation to be measured by colorimetric assay. Together, these studies will quantify the flu virus-specific T-cell responses after vaccination.

Adjuvant-enhanced humoral and cell mediated immune responses to the flu vaccine is expected to confer superior protection against lethal viral infection compared to mice immunized with flu vaccine alone. For these experiments, we will substitute heat inactivated mouse-adapted flu virus (H1N1 influenza virus, strain AlPuerto Rico/8/34 (PR8; VR-95; American Type Culture Collection) to vaccinate mice, due to the limited virulence of human flu viruses in mice. Mice will then be challenged with live flu 42 weeks after initiating the vaccination protocol described above. To infect mice, they will be anesthetized by an intraperitoneal injection of ketamine and xylazine, followed by intranasal administration of flu virus in a 30 $\mu$L volume, using the high dose of $5\times10^6$ of the half-maximal tissue culture infectious dose of virus per mL per mouse, as outlined in a published protocol (Lin, K. L., et al. *J. Immunol.* 2008, 180, 2562-2572). Survival of mice after challenge will then be determined by monitoring mice for significant body weight loss and other indicators that humane endpoints have been reached. These results are expected to allow us to determine if mice given the heparin-chitosan particles as adjuvant are better protected against a virulent influenza challenge. Finally, toxicity in mice will be evaluated. Mice co-administered with seasonal flu vaccine and the nanoparticles loaded with cytokines will be monitored periodically for loss in body weight and changes in body temperatures. We will also examine the site of vaccine administration at various time intervals for signs of pathology. Cumulatively, these studies are expected to demonstrate the value of DLN-targeting nanoparticles as a powerful adjuvant, validating this technology for use in applications such as boosting immunity to the seasonal flu vaccine in the elderly population who are often refractile to this vaccine.

Example 7. Immunosenescence in Elderly Mice

Figure 17:
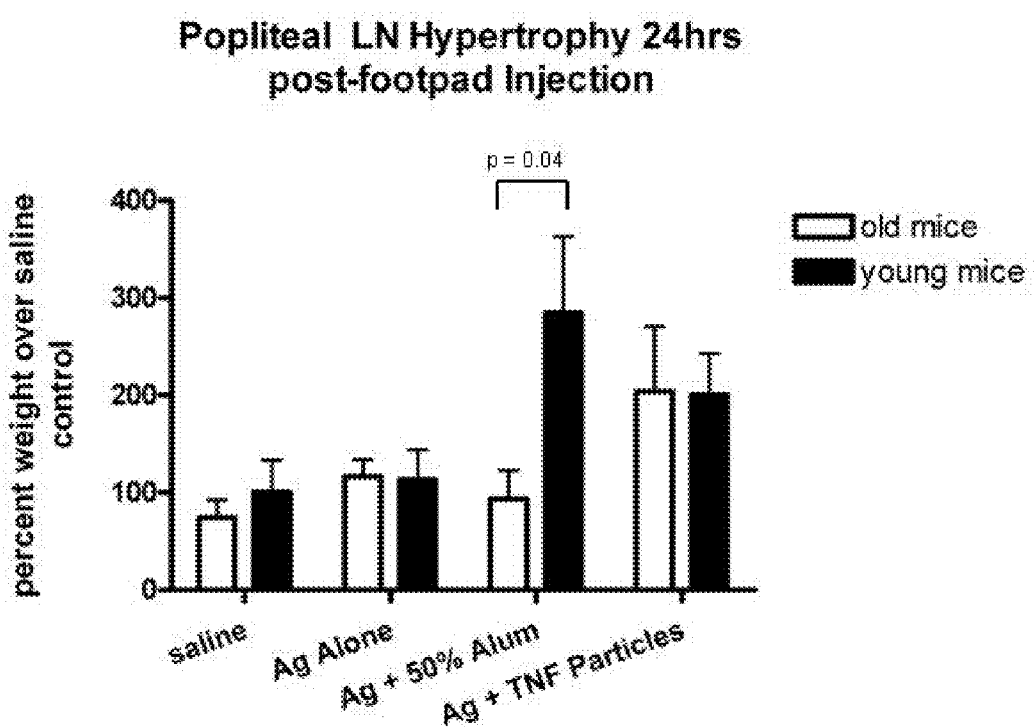
FIG. 17 is a graph of hypertrophy (percent increase over contralateral saline control) in young adult and elderly mice 24 hours after vaccination with saline, antigen alone, antigen plus alum, or antigen plus TNF nanoparticles.

We have observed that co-injecting TNF loaded nanoparticles along with vaccine antigen can potentially overcome immunosenescence in elderly mice by co-injecting TNF loaded nanoparticles along with vaccine antigen (FIG. 17). We demonstrated that rapid swelling of draining lymph nodes following immunization is indicative of a vigorous immune response. Using lymph node hypertrophy as a convenient indicator of immune competency, we examined the effect of immunizing old and young mice using TNF-loaded nanoparticles. It was found that the well-known adjuvant, alum, had a powerful lymph node hypertrophic effect in young but not elderly mice (FIG. 17). In FIG. 17A are numbers of IFN-γ producing T cells in DLNs quantified by flow cytometry 24 hours after footpad injection of soluble OVA alone, or with empty particles, soluble IL-12, or particulate IL-12, and FIG. 17B is a histogram representing IFN-γ expression in CD3+ T cells administered soluble OVA with either soluble or particulate delivery of TNF. FIG. 17 shows evidence of lymph node hypertrophy (represented as percent increase over contralateral saline control) in young adults (2 months) and elderly (>20 months) mice, 24 hours after vaccination with saline, antigen alone, antigen plus alum, or antigen plus TNF-nanoparticles. Antigen alone compared to alum in young mice is significant but not for old mice, antigen alone compared to TNF particles is significant for both old and young mice, particulate TNF is more effective than alum for old mice, and particles alone did not cause hypertrophy. Interestingly, we found that cytokine loaded particles triggered lymph node hypertrophy in young as well as elderly mice, indicating that this adjuvant technology can potentially mitigate immunosenescence and can be useful in developing adjuvant strategies to enhance immune potency of season flu vaccine in the elderly.

Example 8. Particle Design and Construction as Modeled after MC Granules

Figure 18:
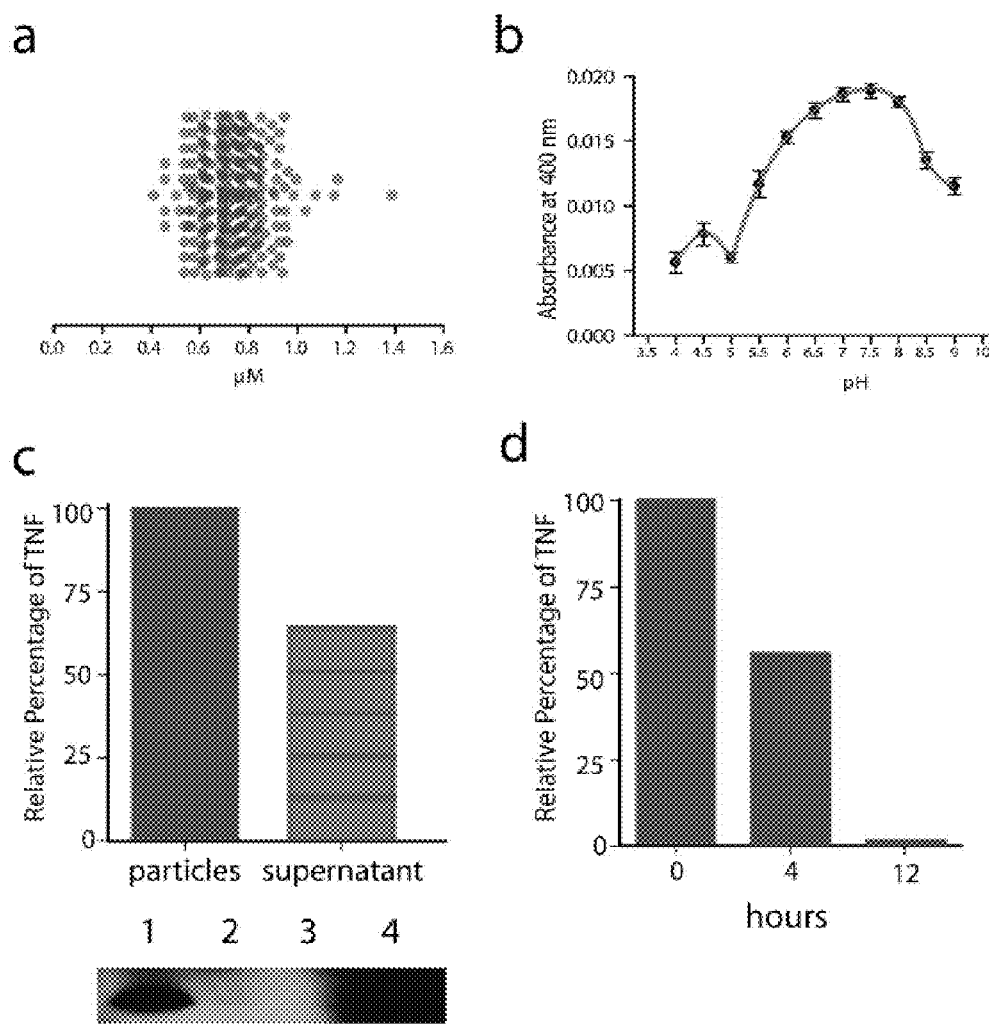
FIG. 18A is a histogram of the sizes of the nanoparticles.
FIG. 18B is a graph of the stability (absorbance at 400 nm) of the particles over various pHs.
FIG. 18C is a graph of the amount of TNF encapsulated in the nanoparticles as compared to the TNF in the supernatant.
FIG. 18D is a graph of the amount of TNF encapsulated in the nanoparticles over time.

To most closely approximate the particles that MC release during the process of degranulation and replicate their efficient LN targeting, we engineered particles to be comprised of heparin, but complexed with chitosan, a non-immunogenic carbohydrate, derived from crustacean shells, that has significant technical advantages over other positively charged compounds. For example, return of a solution containing chitosan to neutral pH also returns the chitosan, itself, to neutral charge, halting the further aggregation of the particles in suspension. These components are both biocompatible and biodegradable. Particles modeled after MC granules were formed by gradually adding a solution of heparin to a solution of chitosan in the presence of the cytokine, TNF, at acidic pH. Since chitosan becomes protonated at acidic pH, giving it a positive charge, modulation of the pH can influence the extent of complexation, control the size of aggregates, and ensure the stability of particles when the solution is returned to neutral pH. Optimizing this parameter resulted in stable particles of relatively uniform size that closely approximated the size of MC-derived particles. The average size of these particles was just under 1 μm (FIG. 18A). The particles were stable well within the range of physiologic pH and only began to become disrupted, as determined by optical density, at the extremes of acidic or basic conditions (FIG. 18B). A small peak occurred in this curve around pH 4.5, which was the optimal pH for the formation of the particles and should designate the pH in the curve where aggregates were able to form (FIG. 18B). The particles, therefore, appeared to be the correct size to resemble MC-derived particles and be stable under circumstances approximating physiological conditions.

After extensive washing of the particles, we used western blot analysis to demonstrate that the particles were capable of encapsulating TNF (FIG. 18C). Furthermore, we found that TNF was slowly released from particles, and was detectable in the supernatant after overnight incubation, but not the 3rd wash from just after particle construction (FIG. 18C), suggesting it was initially retained before appearing in the supernatant. Not only was increasing TNF detectable in the supernatant after clearing it of the particles in suspension (after incubation, FIG. 18C), but there was also a decrease in the amount of TNF in particles over time, collectively supporting the belief that these particles slowly released their cargo into soluble form (FIG. 18D).

Example 9. Synthetic Particles Flow Freely to the Draining LN

Figure 19:
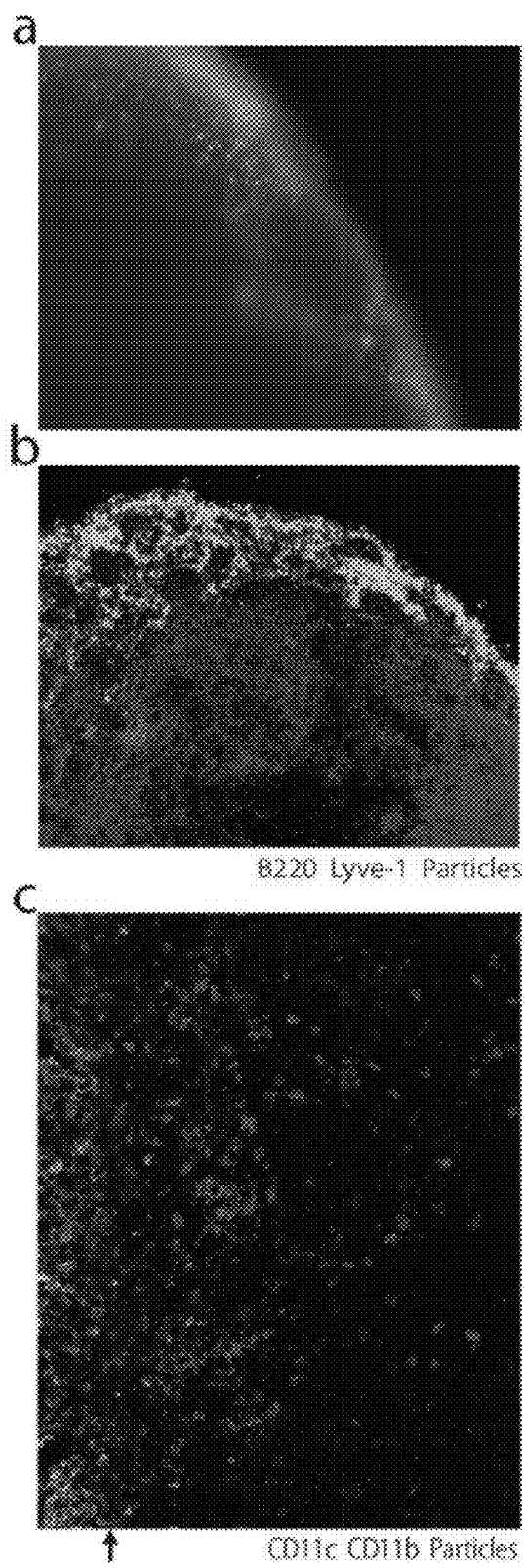
FIG. 19A is an epifluorescence image in whole mount of nanoparticles in LN after peripheral injection of the particles containing FITC-PLL.
FIG. 19B is a confocal microscopy image of a LN isolated 45 minutes post-particle injection, sectioned, and stained for B cells and LN sinuses.
FIG. 19C is a confocal microscopy image of a LN isolated 30 min after injection of particles containing FITC-PLL and stained for CD11c and CD11b.

To determine if our synthetic particles could replicate the functions and in vivo LN-targeting characteristics of natural MC-derived particles, we injected these particles into the rear footpads of mice, prior to isolating and examining the draining popliteal node for their presence. In order to visualize the particles, we added a small amount of poly-L-lysine conjugated to the fluorochrome, FITC, (PLL-FITC) to the reaction as the particles were being formed. As a result, our particles were highly fluorescent and could be visualized in tissues by epifluorescence in whole mount (FIG. 19A) and by confocal microscopy after sectioning (FIG. 19B). Shown in FIG. 19A are particles containing FITC-PLL visualized just under the LN capsule in an image of a LN after peripheral injection with particles containing FITC-PLL. Shown in FIG. 19B is a LN isolated 45 minutes post-particle injection, sectioned and stained for B cells (B220) and LN sinuses (Lyve-10). The particles appeared to be predominantly localized within the sinuses. Footpad-injected PLL-FITC particles quickly traveled to the draining LN, where they can be seen in the subcapsular and medullary sinuses within minutes and with visually striking quantities apparent within 45 minutes (FIG. 19B). These appeared in a distribution pattern similar to that of peripherally released MC-derived particles, which were previously visualized within the LN sinuses. These particles would also slowly release their cytokine cargo in vivo under physiological conditions since the experiments to investigate the kinetics of TNF time release were performed at neutral pH, at 37° C., and in phosphate buffered saline (FIG. 19C), which would approximate the biochemical characteristics of the environment in vivo and within the LN.

Additionally, although some of these particles could be found inside cells, including DCs (as determined by their expression of CD11c) most of the particles in the LN were extracellular (FIG. 19C). Shown in FIG. 19C is a LN isolated 30 minutes after injection of particles containing FITC-PLL and stained for CD11c and CD11b to identify populations of phagocytic cells. Most particles were extracellular, although some co-localized with cells. In FIG. 19C, the arrow points to a line of macrophages that are situated along the subcapsular sinus. The subcapsular sinus is positioned to the left of this macrophage line and contains large numbers of DCs. Macrophages have been previously reported to line the subcapsular sinuses in the draining LN18 and to acquire antigen from their location there, yet images of LNs containing these synthetic particles would suggest that DCs are much more efficient in taking up particles than macrophages within the LN (FIG. 19C). Since this image was acquired only 30 minutes after peripheral injection of particles, there should not be sufficient time for DC homing to LNs, which occurs significantly to the popliteal node from the footpad only by 3 hours after a peripheral insult. As a result, it appeared that those particles that were found inside phagocytic cells were taken up within the LN (FIG. 19C). This established the potential of the synthetic particles to travel to the draining LN.

Figure 20:
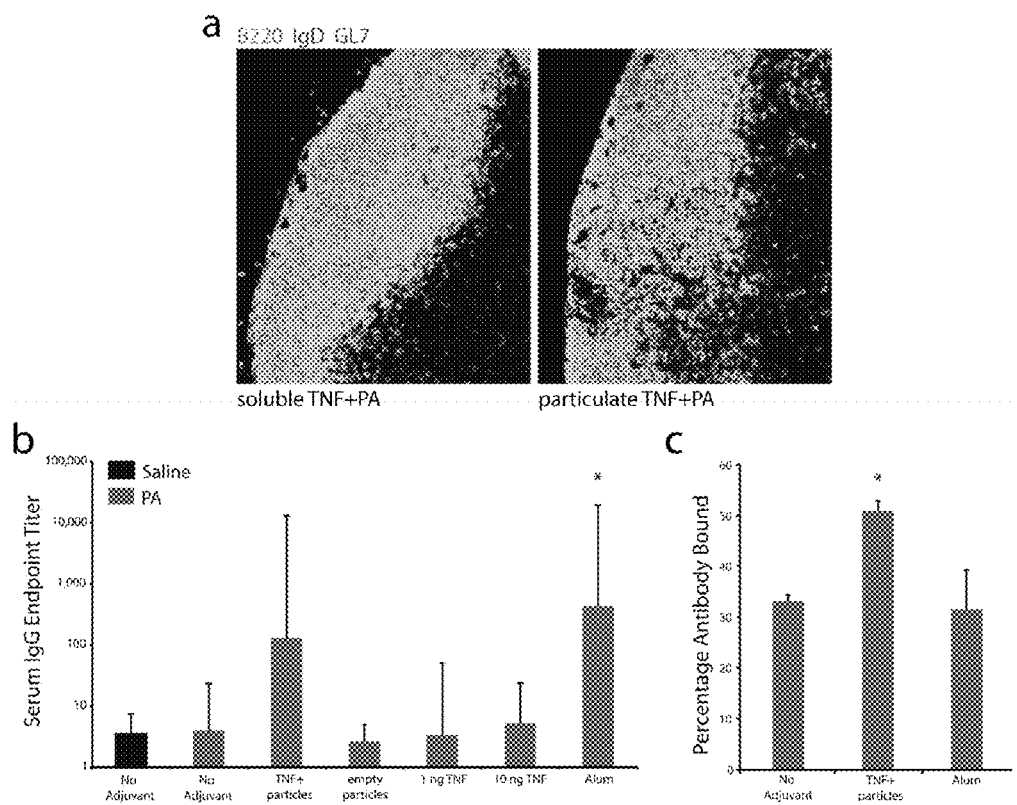
FIG. 20A are lymph node sections from mice injected with 1 μg of protective antigen (PA) of Bacillus anthracis in combination with 1 ng of soluble TNF or <1 ng of encapsulated particulate TNF, isolated 10 days after vaccination, and stained for B cells (B220, green) and IgD (blue) and GL7 (Red) to reveal germinal center activity.
FIG. 20B is a graph of day 21 serum endpoint titers after vaccination with PA in combination with the designated adjuvants with a boost at day 14.
FIG. 20C is a graph of the percentage of antibody that remained bound to the plate after stringent washing, compared to normal ELISA washing.

Example 10. Nanoparticles Affect B Cell Follicles of Lymph Nodes and Promote Antibody Production The cytokine-loaded nanoparticles described in the Example above were used as adjuvants to (a) directly affect the B cell follicles of lymph nodes; and (b) promote antibody production (FIG. 20). Shown in FIG. 20A are lymph node sections from mice injected with 1 μg of protective antigen (PA) of Bacillus anthracis in combination with 1 ng of soluble TNF or <1 ng of encapsulated particulate TNF, isolated 10 days after vaccination. Sections were stained for B cells (B220, green) and IgD (blue) and GL7 (Red) to reveal germinal center activity. FIG. 20B shows day 21 serum endpoint titers after vaccination with PA in combination with the designated adjuvants with a boost at day 14. The average for TNF-containing particles was higher than other groups besides Alum. As shown in FIG. 20C, serum was tested at concentrations 2-fold over the endpoint titer to determine antibody avidity by adding a stringent wash step using 1 M ammonium thiocyanate. The graph represents the percentage of antibody that remained bound to the plate after stringent washing, compared to normal ELISA washing. The avidity of antigen-specific antibodies was highest using particulate TNF as an adjuvant (p<0.05), and did not differ between antigen alone and Alum. The antibodies generated during vaccination were of greater avidity than the currently approved adjuvant, alum (FIG. 20C).

Figure 21:
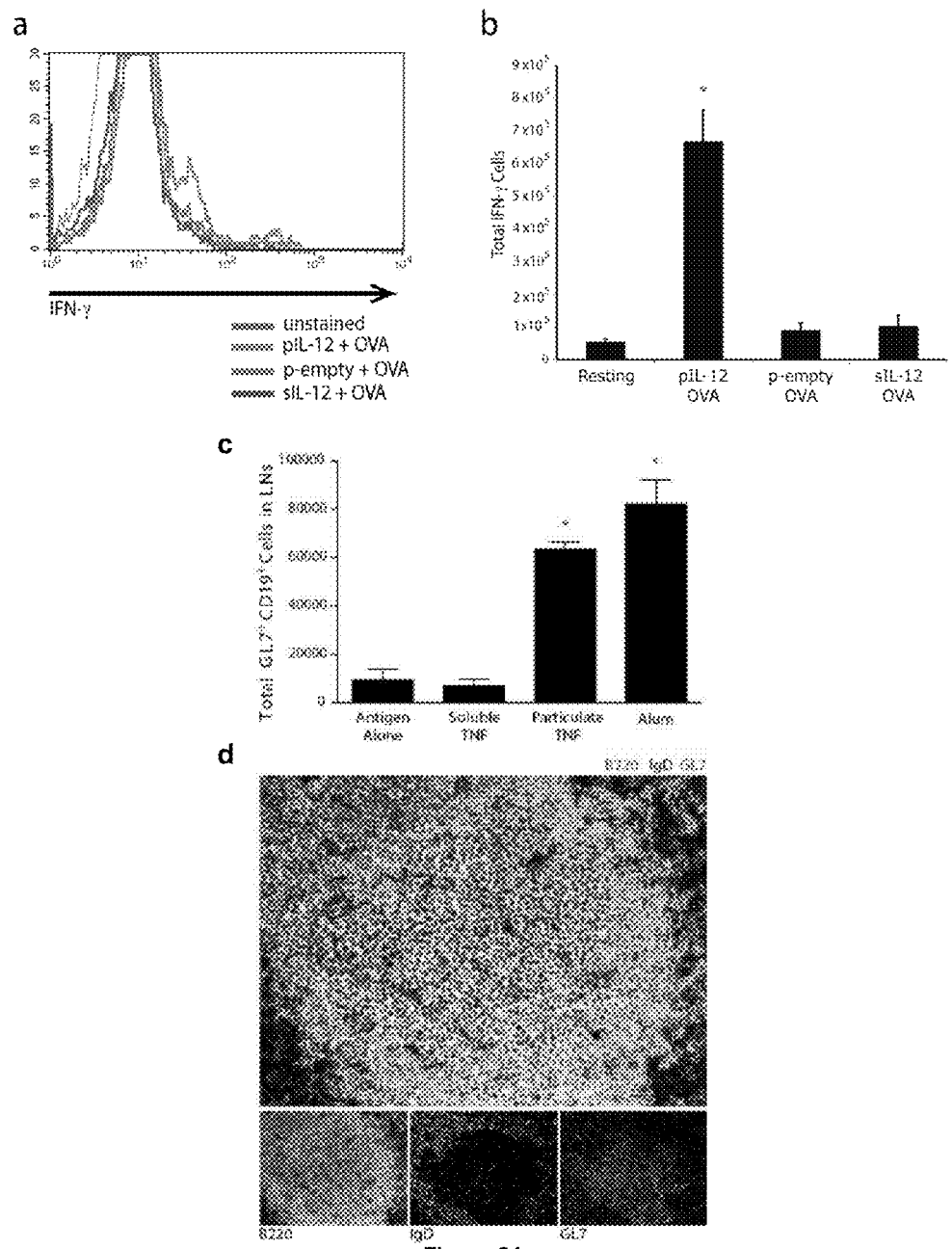
FIG. 21A shows IFN-γ production in draining lymph node T cells, 24 hours after vaccination with OVA, soluble IL-12 (sIL-12) with OVA, particulate IL-12 (pIL-12) with OVA, or empty particles (p-empty) with OVA.
FIG. 21B is a graph of the total numbers of IFN-γ positive T cells within draining lymph nodes.
FIG. 21C is a graph of the number of activated B cells after immunization with various samples.
FIG. 21D are images of sections of draining LN isolated 10 days after vaccination with HA in combination with particulate TNF.

We were also able to use the particles to skew the resulting adjuvant activity, in this case by polarizing T cell responses towards a "Th1 type response", defined by increased production of IFN-γ by T cells (FIG. 21). These results were achieved through differential loading of particles with additional cytokines beyond TNF, in this case IL-12 (FIG. 21). For this study, mice were immunized with soluble antigen (ovalbumin) and particles containing TNF or IL-12, as adjuvant. To determine levels of IFN-γ produced by T cells, lymph nodes were isolated and single cell suspensions were produced. These cells were then stained for T cell marker, CD3, and intracellularly for IFN-γ. Intracellular IFN-γ production in T cells was then determined by flow cytometry. FIG. 21A shows delivery of particulate IL-12 (pIL-12) enhanced IFN-γ production in draining lymph node T cells, 24 hours after vaccination with OVA, in contrast to soluble IL-12 (sIL-12) with OVA or empty particles (p-empty) with OVA. FIG. 21B shows quantification of the total numbers of IFN-γ positive T cells within draining lymph nodes.

LNs were examined to determine if particulate TNF in combination with an antigen could induce germinal center formation. For this study, mouse footpads were injected with a vaccine formulation containing the soluble experimental antigen (HA from Flu) alone or in conjunction with synthetic particles containing TNF. Responses were also compared to mice that were administered HA in the standard vaccine adjuvant (Alum) as a positive control. As an additional control, some mice were given HA in combination with empty particles, consisting of only the heparin-chitosan core without TNF. We then stained single cell suspensions of B cells (CD19) from the draining LN for the cellular activation marker of germinal centers, GL7, and quantified the presence of this marker by flow cytometry. In this study, Alum displayed expected adjuvant activity, indicated by increased numbers of GL7+ B cells in draining LNs, 10 days after vaccine administration (FIG. 21C). Similarly, our experimental adjuvant of TNF-loaded nanoparticles also increased the numbers of germinal center B cells (FIG. 21C). To visually confirm this quantitation of germinal center B cells in those mice given antigen in conjunction with particulate TNF, we stained LN sections for B cell follicles and evidence of structures with germinal center morphology at 10 days (FIG. 21D, stained for B220, IgD, and GL7). The draining LN section was isolated 10 days after vaccination with 1 μg of HA in combination with <1 ng of encapsulated particulate TNF. In these areas, the cellular activation marker of germinal centers, GL7, was present and a characteristic reduction in IgD staining on B cells, as occurs within activated germinal center B cells, was observed within B cell zones (FIG. 21D). We also observed similar results, in that particulate TNF induces germinal center formation, using a bacterially-derived antigen, protective antigen (PA) from Bacillus anthracis (data not shown). These findings suggest that particulate TNF is sufficient to promote the production of germinal centers when administered in conjunction with a dose of antigen that would not otherwise induce their formation.

Example 11. Neutrophil Recruitment

Figure 22:
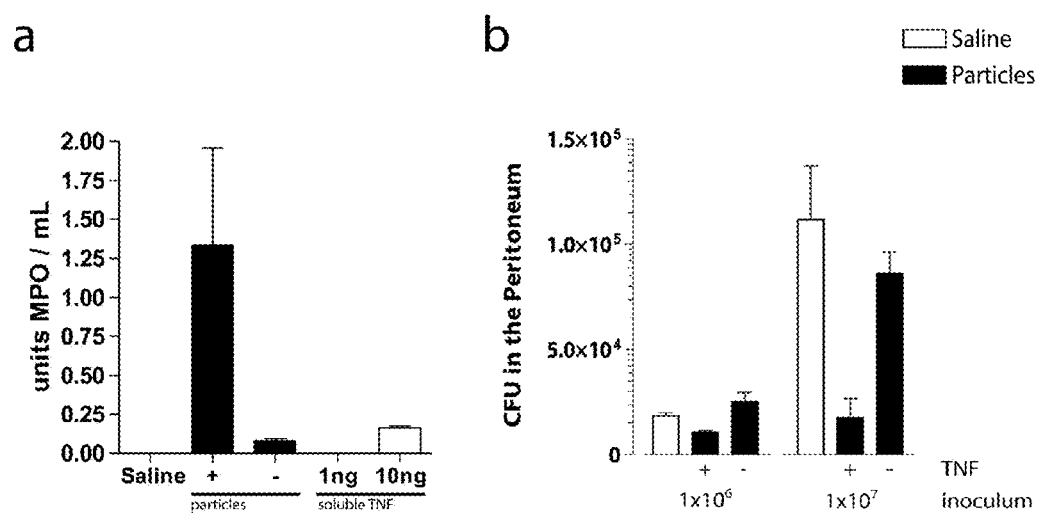
FIG. 22A is a graph of recruitment of neutrophils upon injection of particles with TNF, compared to control particles or soluble TNF, extending the efficacy of TNF greater than 10-fold.
FIG. 22B is a graph showing that the injection of particles containing TNF after infection with *Staphylococcus aureus* enhances the host's ability to clear bacterial infection significantly.

The cytokine-loaded nanoparticles described in the Example above can be used therapeutically to promote innate immune responses, such as neutrophil recruitment and clearance of bacteria during an experimental model of Staph infection (FIG. 22). Mice were injected peritoneally with saline, empty particles alone, particles containing a maximum of 1 ng of TNF (FIG. 22A), or 1 ng or 10 ng of soluble TNF, after which mice were sacrificed and the peritoneum was washed to remove the cellular contents. An assay to determine the amount of neutrophil influx into the peritoneum, based on detection of neutrophil product myeloperoxidase, was then performed. As shown in FIG. 22B, particles were injected into the peritoneum after infection with Staph aureus bacteria. Two different doses of bacteria, $1 \times 10^6$ and $1 \times 10^7$ were used in this study. After infection, mice were given a "treatment" of saline alone, empty particles, or particles containing TNF. Only particles containing TNF significantly accelerated the clearance of bacteria compared to sham, saline treatment.

Example 12. The Effectiveness of Particulate Adjuvant Against a Lethal Viral Infection (Flu)

It was investigated whether the adjuvant activity of MC granules could be similarly recapitulated by the engineered particles. To begin, we examined antibody production in response to a soluble antigen (HA derived from Flu) injected with particulate TNF or soluble TNF. To compare antibody quality after vaccination with our experimental adjuvant to a known adjuvant, we included a positive control of HA emulsified in the standard vaccine adjuvant (Alum). Mice were vaccinated, followed by a boost at 14 days, and serum was collected at 21 days to assess the resulting antibodies. When we measured total HA-specific IgG responses, we observed that particulate TNF, but not soluble TNF, displayed adjuvant activity, as evidenced by significantly increased antibody titers over antigen-alone vaccination, which were comparable those elicited by the adjuvant Alum (FIG. 23A), which was used as a positive control. However, we found that for both IgG1 and IgG2a antibody subclasses, particulate TNF produced significantly increased antibody titers over antigen-alone vaccination (FIG. 23B) while, in contrast, Alum promoted augmented IgG1 but not IgG2a endpoint titers after vaccination (FIG. 23C). This observation illustrated that particulate TNF may have additional advantages over alum, promoting a more broad specific antibody response. Unique antibody subclasses have been show to have unique activities in vivo and differing effectiveness against individual challenges; therefore, the ability to promote antibody diversity is a key attribute to this novel adjuvant system.

Since germinal centers are key for refining the adaptive immune response and thought to be responsible for the generation of high specificity antibody and since we observe that they are promoted by particulate TNF (see FIG. 21), there may be functional improvements in antibody quality after vaccination using particulate TNF as an adjuvant. To examine antibody avidity produced in our vaccination studies, we used a modified ELISA procedure based on several published studies. In this assay, serum was first incubated with antigen-coated ELISA plates, followed by washing with either normal ELISA wash buffer alone or buffer containing varying concentrations of ammonium thiocyanate. Those serum samples with higher avidity interactions retained more bound antibody than samples with lower avidity interactions during the stringent washing with ammonium thiocyanate. After this washing step, normal ELISA detection proceeded with standard protocols. With the resulting data, the percentage of antibody that remained bound after washing with a given ammonium thiocyanate concentration was determined. We found that the avidity of the antigen-specific antibodies that were present was much higher for mice given HA and particulate TNF, compared to mice given HA alone or with alum, the latter two of which were not dissimilar (FIG. 23D).

Use of HA as our experimental antigen also made it possible for us to assess if our novel adjuvant system conferred any protection to the host in a lethal challenge model of Flu. For this study, mice were vaccinated as described previously, followed by challenge with a mouse virulent strain of Flu. When mice were then monitored daily for survival, we observed that vaccination with HA in conjunction with particulate TNF significantly increased survival of mice after Flu challenge (FIG. 23E). This indicated our particulate cytokine delivery system is an effective novel adjuvant that can be used to confer protection from an infectious challenge. Cumulatively, these studies demonstrated that this particulate TNF delivery system promotes both high magnitude (FIG. 21) and affinity (FIG. 23D) antibodies as part of an adaptive immune response that can be protective, as in the case of a lethal Flu challenge (FIG. 23D), and this response is possible through the potentiation of adaptive responses within the LN microenvironment (FIG. 21).

Figure 23:
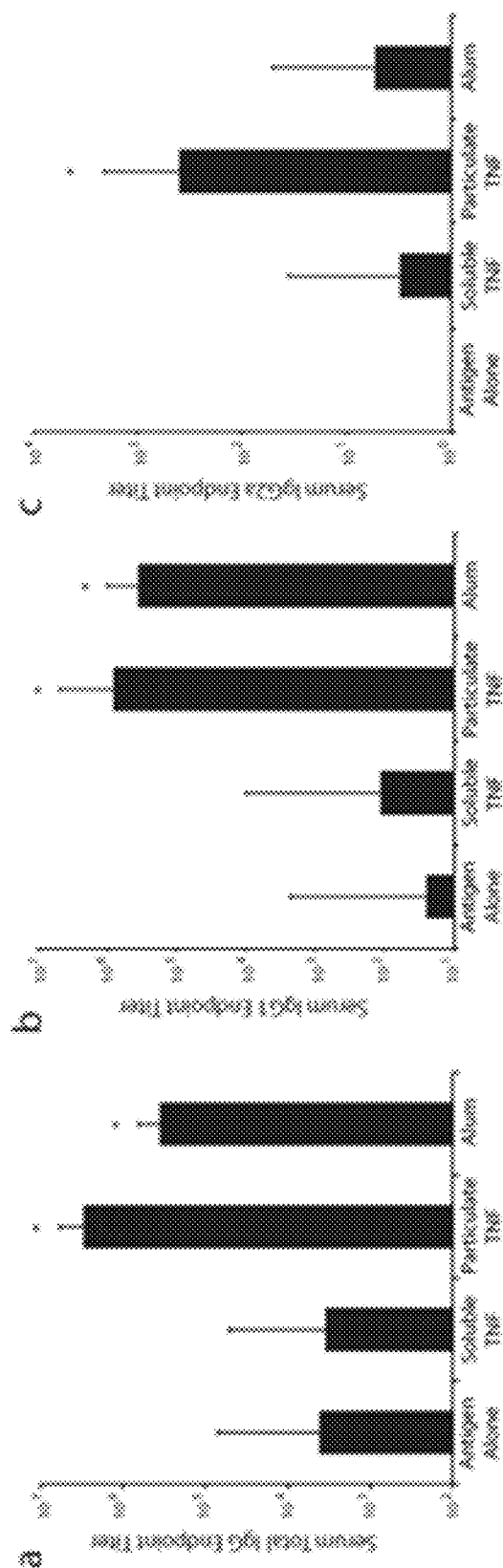
FIG. 23 are graphs showing serum total IgG (A), serum IgG1 (B), and serum IgG2a (C) after vaccination with HA in combination with various adjuvants.
Figure 23:
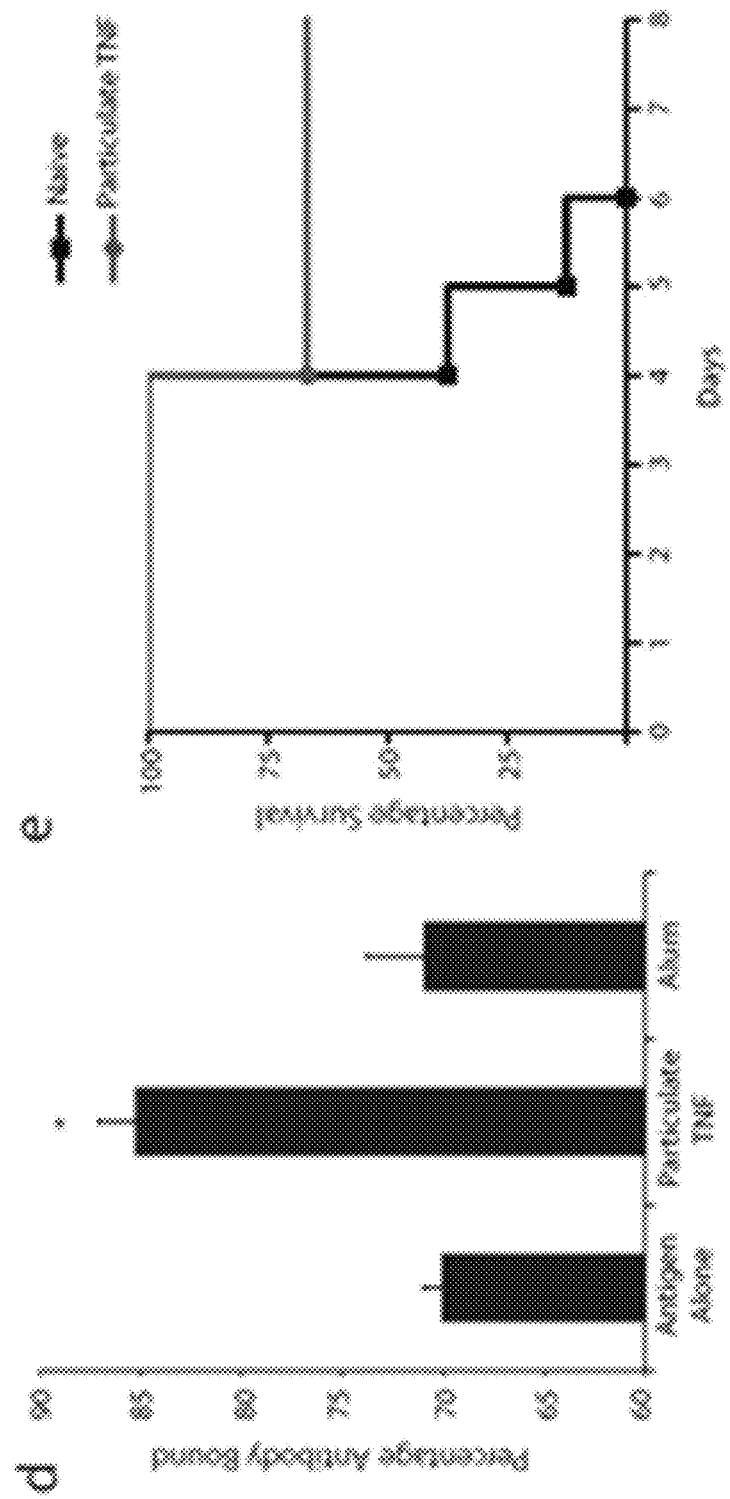

Shown in FIG. 23 are day 21 geometric titers for (A) total IgG, (B) IgG1, and (C) IgG2a after vaccination with HA in combination with the designated adjuvants, with a boost at day 14. Significance was determined by one-way ANOVA with Dunne post test to compare groups to the antigen alone group. Significance is represented by * where $p<0.05$. Error bars represent the standard deviation. Shown in FIG. 23D is data for day 21 serum after vaccination with HA in combination with the designated adjuvants, with a boost at day 14 to determine antibody avidity by washing ELISA plates with 0.25 M ammonium thiocyanate. The graph represents the percentage of antibody that remained bound to the plate after stringent washing, compared to normal ELISA washing. The avidity of antigen-specific antibodies was highest using particulate TNF as an adjuvant ($p<0.05$), and did not differ between antigen alone and Alum. Shown in FIG. 23E is data for mice vaccinated as in (A)-(B) were challenged intranasally with a lethal dose of H1N1 Flu on day 35 ($8 \times 10^4$ TCID-50 per mouse). Survival was monitored daily to generate the plot. Curves differ significantly with $p=0.007$ by the logrank test.

Figure 24:
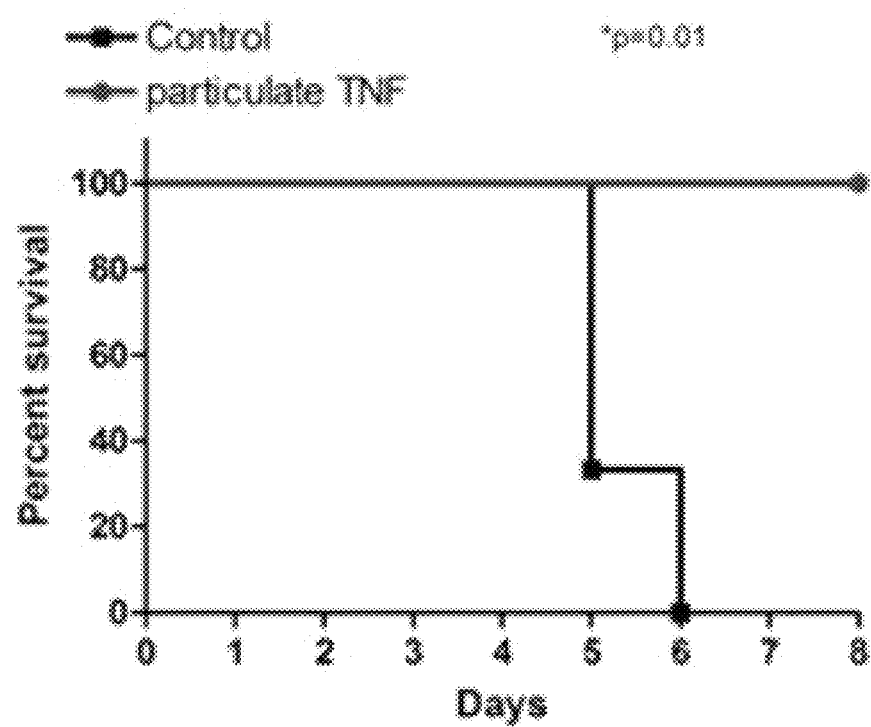
FIG. 24 is a graph of survival of aged mice vaccinated with TNF-nanoparticles and vaccine versus those vaccinated with particulate TNF and challenged with H1N1 flu.

Example 13. TNF-Loaded Nanoparticles can Protect Aged Mice from a Lethal Influenza Challenge Aged mice were immunized with a novel vaccine formulation, TNF-loaded nanoparticles in combination with the H1N1 Influenza vaccine antigen, 2 and 4 weeks prior to a lethal challenge with mouse-adapted H1N1. As shown in FIG. 24, the survival of mice was significantly longer in mice immunized with particulate TNF ($p<0.05$) with 100% survival post 1 week, demonstrating the ability of aged mice to be effectively protected from influenza.

Example 14. Effectiveness as a Therapeutic

Figure 25:
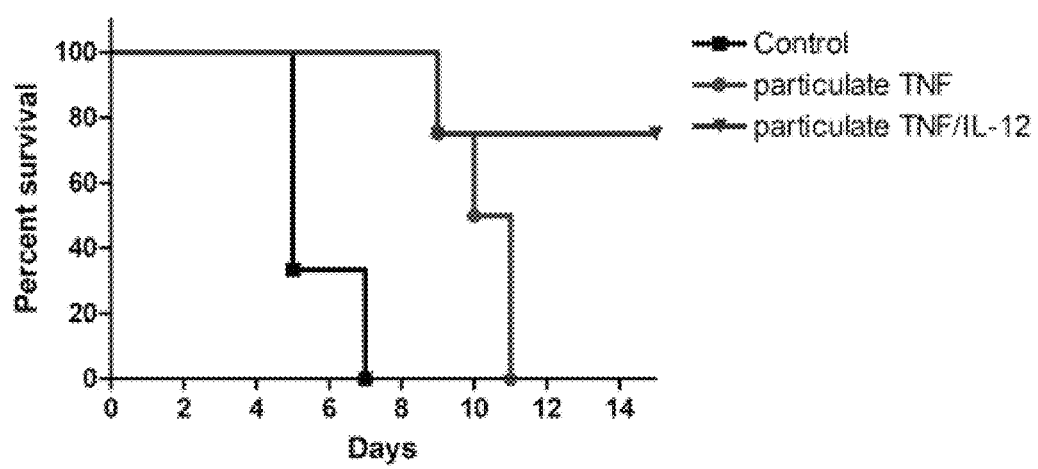
FIG. 25 is a graph of survival of aged mice challenged with H1N1 flu and then immunized with H1N1-TNF-nanoparticles or H1N1-TNF-IL12-nanoparticles or none.

As shown in FIG. 25, vaccine formulations comprising inactivated Flu virus plus TNF-loaded or TNF/IL-12 loaded nanoparticles has therapeutic potential even after infection has been initiated in aged mice. Aged mice were challenged with mouse adapted H1N1 Influenza virus, and 24 hours later subcutaneously immunized with a novel vaccine formulation comprising of inactivated H1N1 Influenza virus plus TNF-loaded nanoparticles or TNF/IL-12 loaded nanoparticles. Compared to aged control unimmunized mice, the survival of mice was significantly longer in mice immunized with particulate TNF ($p<0.05$). The protection was even more remarkable when TNF/IL-12 loaded nanoparticles were used. As much as 80% of mice were protected from lethal infection in excess of 14 days.

We claim:

1. A method of treating food allergies comprising administering to a subject a nanoparticle comprising:
   heparin; and
   chitosan,
   wherein the heparin and the chitosan nanoparticle encapsulates IL-12, and
   wherein the nanoparticle is administered by a route selected from oral, sublingual, intramuscular, subcutaneous, intravenous, transdermal, topical, parenteral, buccal, rectal, mucosal, intranasal, injection, inhalation, implant, and a combination thereof.

2. The method of claim 1, wherein the nanoparticle further comprises an antigen, wherein the antigen comprises at least one of a protein, peptide, polysaccharide, lipid, glycoprotein, glycolipid, glycoprotein, lipoprotein, lipopolysaccharide, or a combination thereof.

3. The method of claim 1, wherein the nanoparticle further comprises at least one immunomodulatory agent selected from the group consisting of TNF, IL-1α, IL-2, IL-23, IL-18, IL-10, and IFN.

4. The method of claim 2, wherein the antigen is the substance that provoked the food allergy.

5. The method of claim 1, wherein IgG2a levels are increased in the subject after administration of the nanoparticle.

* * * * *